(12) United States Patent
Katsurada et al.

(10) Patent No.: US 12,257,447 B2
(45) Date of Patent: Mar. 25, 2025

(54) LIGHT IRRADIATION DEVICE AND LIGHT IRRADIATION SYSTEM

(71) Applicant: ASAHI INTECC CO., LTD., Seto (JP)

(72) Inventors: Yuko Katsurada, Seto (JP); Toshihiko Tsukamoto, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 714 days.

(21) Appl. No.: 17/514,961

(22) Filed: Oct. 29, 2021

(65) Prior Publication Data

US 2022/0047884 A1    Feb. 17, 2022

Related U.S. Application Data

(63) Continuation of application No. PCT/JP2020/016881, filed on Apr. 17, 2020.

(30) Foreign Application Priority Data

May 16, 2019   (JP) .................. 2019-092695

(51) Int. Cl.
*A61N 5/06* (2006.01)
*A61B 18/24* (2006.01)
(Continued)

(52) U.S. Cl.
CPC ........... *A61N 5/0601* (2013.01); *A61B 18/24* (2013.01); *A61B 2018/208* (2013.01); *A61B 2018/2272* (2013.01)

(58) Field of Classification Search
CPC .......... A61N 5/0601; A61N 2005/0602; A61N 5/0603; A61B 18/24; A61B 2018/208; A61B 2018/2255; A61B 2018/2272
(Continued)

(56) References Cited

U.S. PATENT DOCUMENTS 5,772,642 A * 6/1998 Ciamacco, Jr. ...... A61N 5/1002
                                                                  604/529
6,283,957 B1    9/2001 Hashimoto et al.
(Continued)

FOREIGN PATENT DOCUMENTS

CN    103108601 A    5/2013
EP    2540247 A1    1/2013
(Continued)

OTHER PUBLICATIONS

Makoto Mitsunaga, et al., "Cancer Cell-Selective in Vivo Near Infrared Photoimmunotherapy Targeting Specific Membrane Molecules", Nature Medicine, vol. 17(12), pp. 1685-1691, Jun. 1, 2012.
(Continued)

*Primary Examiner* — Ahmed M Farah
(74) *Attorney, Agent, or Firm* — Oliff PLC

(57) ABSTRACT

A medical light irradiation device is provided with an elongated main body portion, a light irradiation portion, and a marker portion. The light irradiation portion is provided on one portion of a side surface on a distal end side of a main body portion, and irradiates light towards outside. The marker portion is provided on a distal end side of the main body portion, is radiopaque, and has a shape for identifying the location of the light irradiation portion in a circumferential direction when viewed from the outside.

14 Claims, 14 Drawing Sheets

(51) Int. Cl.
   *A61B 18/20* (2006.01)
   *A61B 18/22* (2006.01)

(58) Field of Classification Search
   USPC .......................................................... 606/15
   See application file for complete search history.

(56) References Cited

U.S. PATENT DOCUMENTS

| | | | |
|---|---|---|---|
| 6,520,959 B1* | 2/2003 | Iwahashi | A61N 5/0601 606/17 |
| 11,874,455 B2* | 1/2024 | Katsurada | A61B 18/18 |
| 2012/0330293 A1* | 12/2012 | Arai | A61N 5/062 606/15 |
| 2018/0008122 A1 | 1/2018 | Arai et al. | |
| 2018/0140804 A1* | 5/2018 | Tsukamoto | A61M 29/02 |
| 2019/0099237 A1* | 4/2019 | Booker | A61B 5/0066 |
| 2022/0047885 A1* | 2/2022 | Tsukamoto | A61B 90/39 |

FOREIGN PATENT DOCUMENTS

| | | |
|---|---|---|
| JP | H07-308393 A | 11/1995 |
| JP | H11-276605 A | 10/1999 |
| JP | H11-276606 A | 10/1999 |
| JP | H11-332876 A | 12/1999 |
| JP | H11-332877 A | 12/1999 |
| JP | 2001509038 A | 7/2001 |
| JP | 2005287832 A | 10/2005 |
| JP | 2007528752 A | 10/2007 |
| JP | 2012100726 A | 5/2012 |
| JP | 2012515603 A | 7/2012 |
| JP | 2014523907 A | 9/2014 |
| JP | 5598935 B2 | 10/2014 |
| JP | 5753573 B2 | 7/2015 |
| JP | 5810507 B2 | 11/2015 |
| JP | 2016154632 A | 9/2016 |
| JP | 2018000867 A | 1/2018 |
| WO | 9729803 A1 | 8/1997 |
| WO | 2005007216 A2 | 1/2005 |
| WO | 2007084608 A2 | 7/2007 |
| WO | 2010086849 A1 | 8/2010 |
| WO | 2013009475 A1 | 1/2013 |
| WO | 2013049491 A1 | 4/2013 |

OTHER PUBLICATIONS

Kazuhide Sato et al., "Spatially Selective Depletion of Tumor-Associated Regulatory T Cells With Near-Infrared Photoimmunotherapy", Science Translational Medicine, vol. 8, Issue 352, pp. 1-12, Aug. 17, 2016.

Shuhei Okuyama et al., "Interstitial Near-Infrared Photoimmunotherapy: Effective Treatment Areas and Light Doses Needed for Use With Fiber Optic Diffusers", Oncotarget, vol. 9, No. 13, pp. 11159-11169, Feb. 16, 2018.

* cited by examiner

Fig. 3
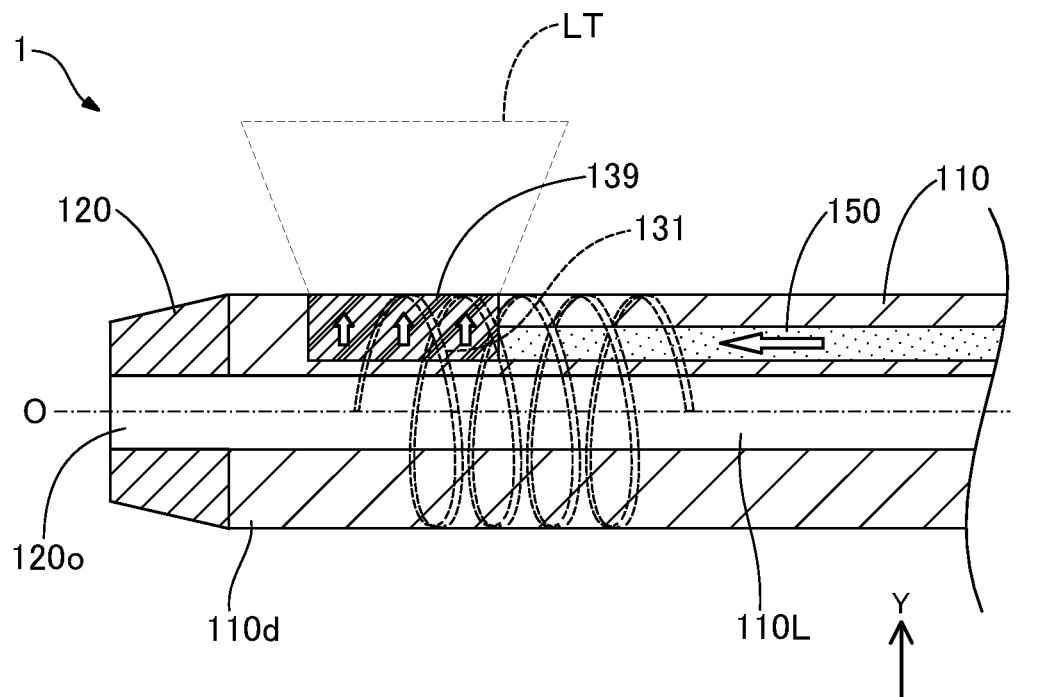
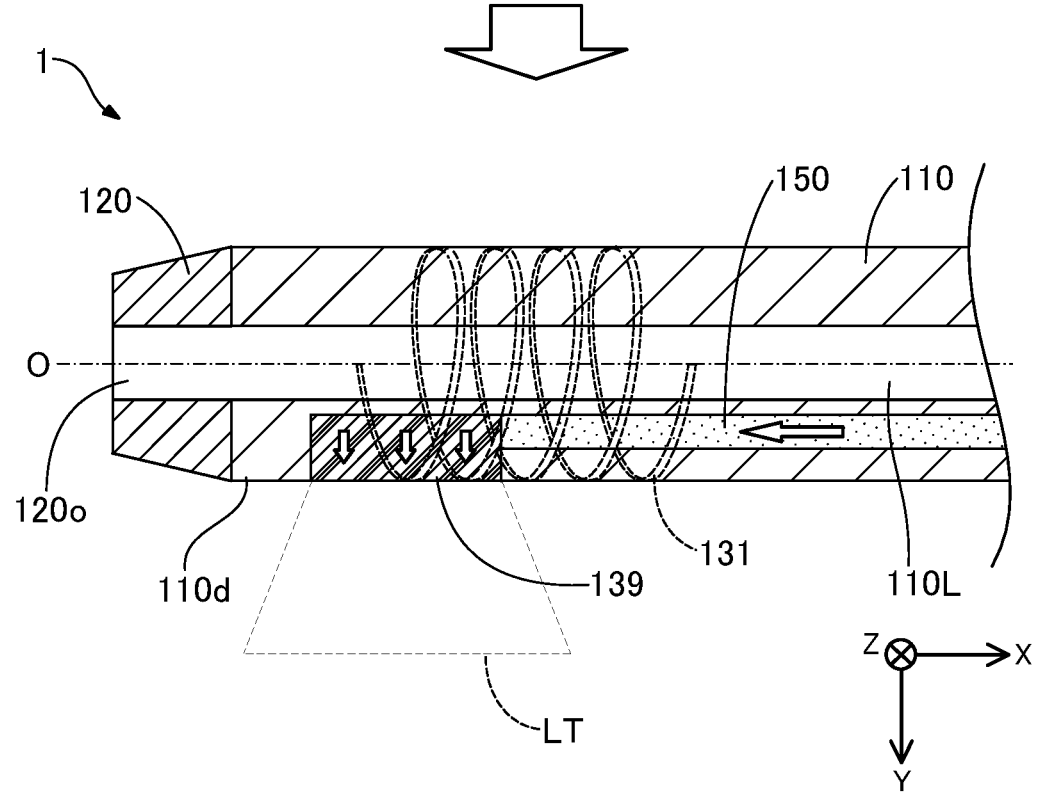

Fig. 7
(A)
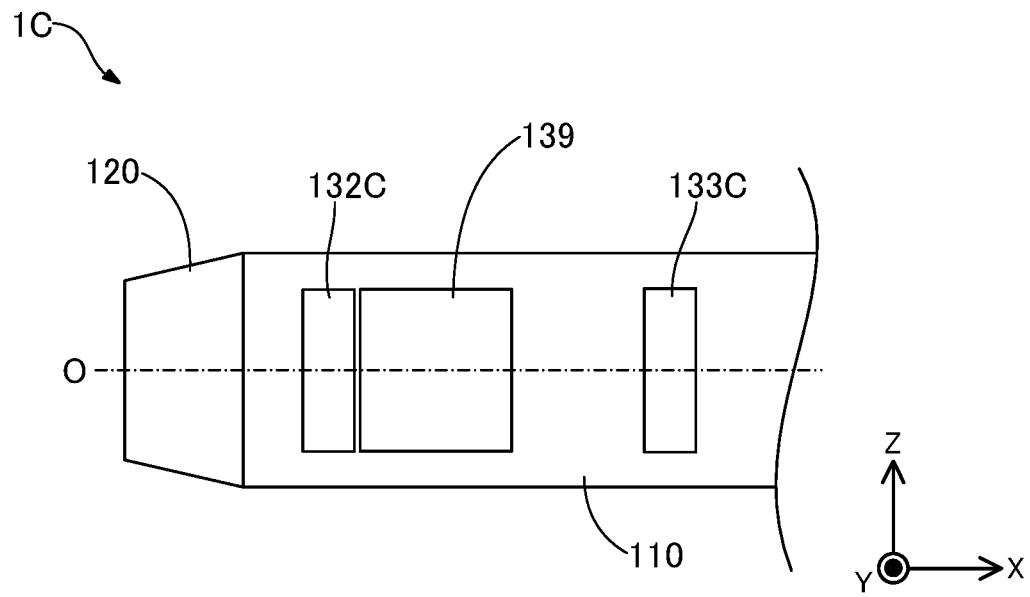
(B)
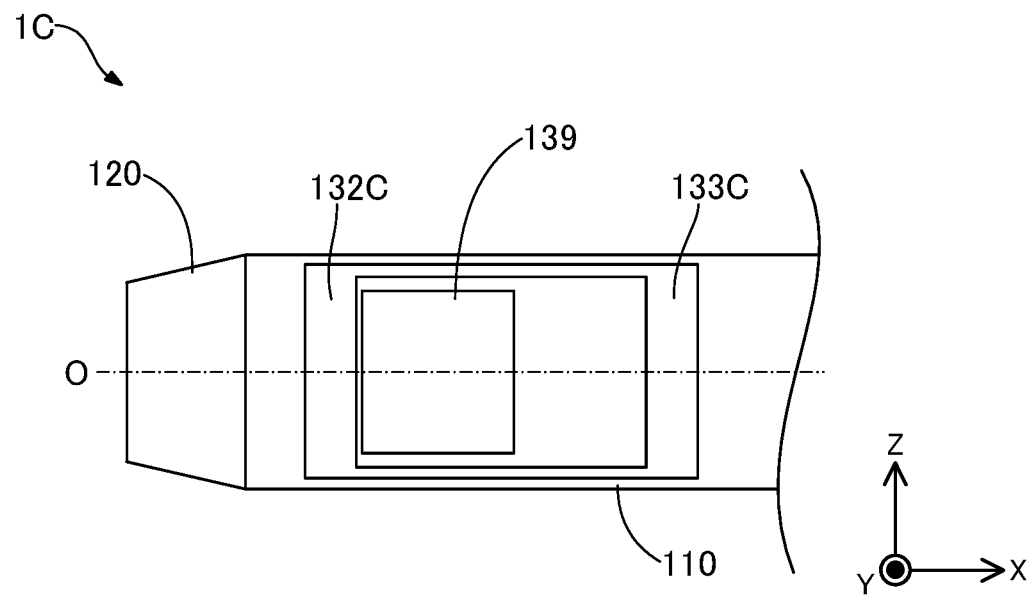

Fig. 12
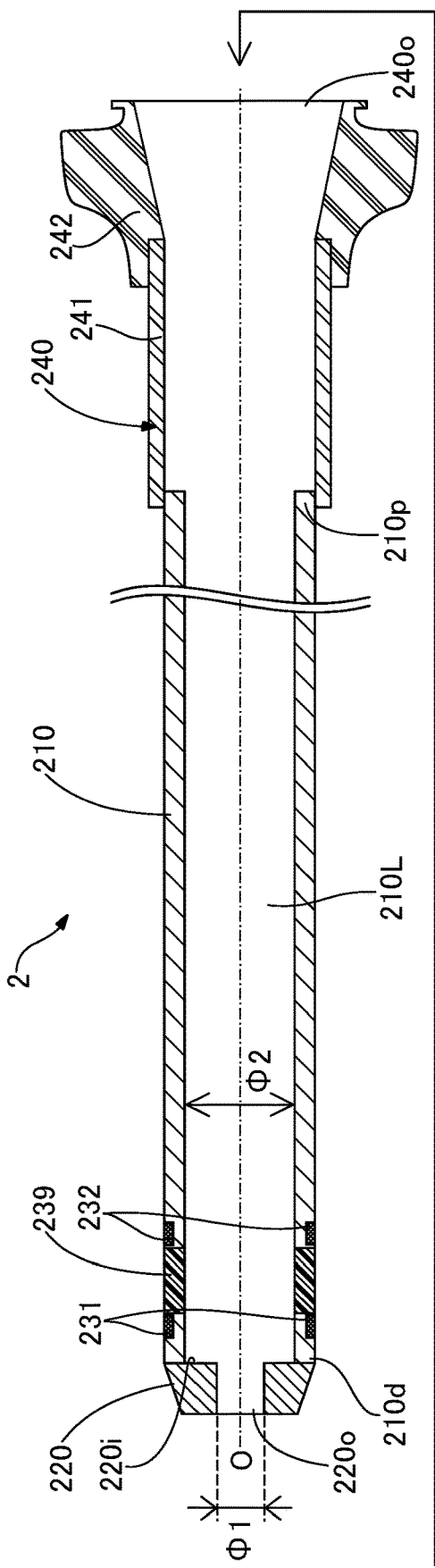
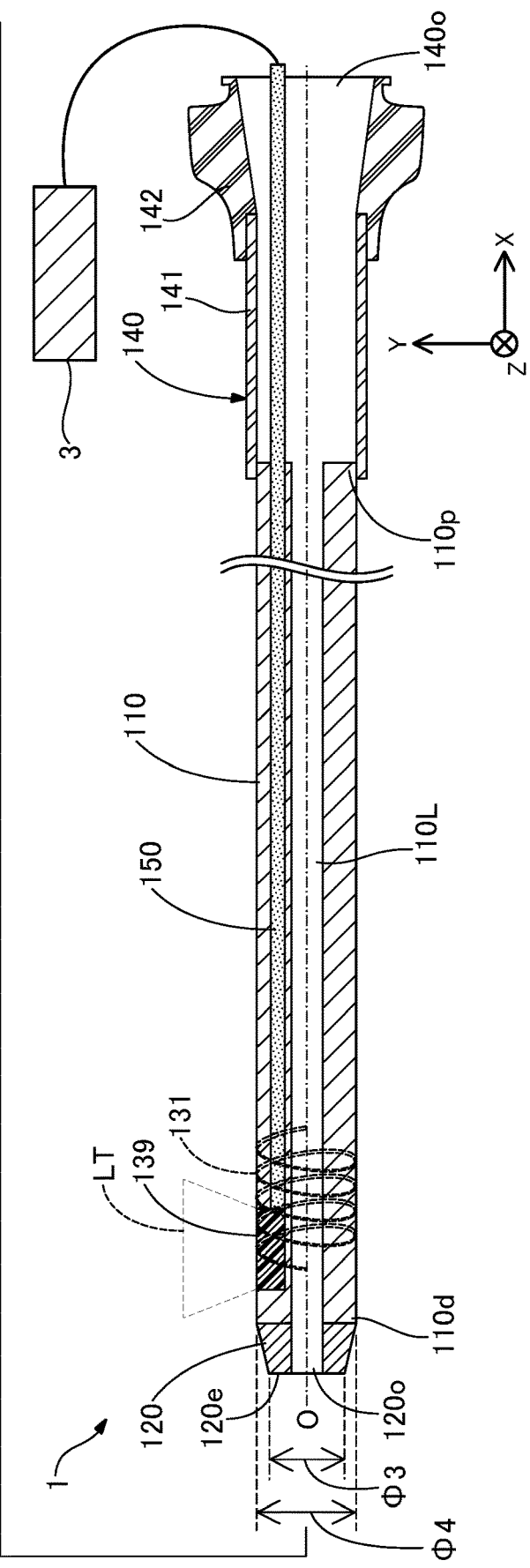

LIGHT IRRADIATION DEVICE AND LIGHT IRRADIATION SYSTEM

The present application is a Bypass Continuation of PCT/JP2020/016881, filed Apr. 17, 2020, which is based upon and claims priority from JP Application No. 2019-092695 filed on May 16, 2019, the entirety of the prior applications being hereby incorporated by reference into this application.

TECHNICAL FIELD

The disclosed embodiments relate to a light irradiation device and a light irradiation system.

BACKGROUND ART

In cancer treatment, surgical, radiological, and pharmacological (chemical) techniques are used alone or in combination with each other, and these techniques have each experienced development in recent years. However, there are many types of cancer for which satisfactory treatment techniques have not yet been found, and there is an expectation that such treatment techniques will be further developed. A technique referred to as PDT (Photodynamic Therapy) is known as a cancer treatment technique. In PDT, a light-sensitive substance is administered intravenously. Then, light irradiation generates a reactive oxygen species in the cancer cells and kills the cancer cells (for example, see Non-Patent Literature 1). However, PDT has not been widely used as a therapeutic technique due to the low accumulation selectivity of light-sensitive substances within cancer cells, and the significant side effects caused by uptake by normal cells.

Further, NIR-PIT (Near-Infrared Photoimmunotherapy) is a treatment technique that has been attracting attention in recent years. NIR-PIT uses a complex in which two compounds, namely an antibody against a specific antigen of the cancer cells and a photosensitive substance (such as IRDye 700DX), are bonded to each other. When this complex is administered intravenously, it selectively accumulates in the cancer cells in the body. Then, by irradiating light of an excitation wavelength of the photosensitive substance in the complex (for example, 690 nm), the complex is activated and exhibits anticancer activity (for example, see Patent Literature 1). NIR-PIT can reduce side effects compared to PDT due to the accumulation selectivity of the antibody toward the cancer, and localized light irradiation. Moreover, because NIR-PIT involves light irradiation in a near-infrared region such as 690 nm (NIR irradiation), effects of the NIR irradiation on the immune system are also expected (for example, see Non-Patent Literature 2).

The predetermined wavelength region illustrated above that includes 690 nm is also referred to as a biological spectroscopic window. This is a wavelength region in which the absorption of light by biological components is lower than in other wavelength regions. However, there is a problem that because the penetration of light is insufficient when the light is irradiated from surface of the body, it cannot be applied to cancers deep inside the body. Therefore, in recent years, NIR-PIT, in which light irradiation is performed from a location close to the cancer cells rather than from the body surface, is being studied (for example, see Non-Patent Literature 3). For example, Patent Literature 2 and Patent Literature 3 disclose devices that can be used in the PDT and NIR-PIT techniques described above. The devices described in Patent Literature 2 and Patent Literature 3 are both used by being inserted into a blood vessel, and are capable of irradiating light deep inside the body.

CITATION LIST

Patent Literature

Patent Literature 1: Japanese Unexamined Patent Application Publication (Translation of PCT Application) No. 2014-523907
Patent Literature 2: Japanese Unexamined Patent Application Publication No. 2018-867
Patent Literature 3: Japanese Unexamined Patent Application Publication (Translation of PCT Application) No. 2007-528752

Non-Patent Literature

Non-Patent Literature 1: Makoto Mitsunaga, Mikako Ogawa, Nobuyuki Kosaka Lauren T. Rosenblum, Peter L. Choyke, and Hisataka Kobayashi, Cancer Cell-Selective In Vivo Near Infrared Photoimmunotherapy Targeting Specific Membrane Molecules, Nature Medicine 2012 17(12), p. 1685-1691
Non-Patent Literature 2: Kazuhide Sato, Noriko Sato, Biying Xu, Yuko Nakamura, Tadanobu Nagaya, Peter L. Choyke, Yoshinori Hasegawa, and Hisataka Kobayashi, Spatially selective depletion of tumor-associated regulatory T cells with near-infrared photoimmunotherapy, Science Translational Medicine 2016 Vol. 8 Issue 352, ra110
Non-Patent Literature 3: Shuhei Okuyama, Tadanobu Nagaya, Kazuhide Sato, Fusa Ogata, Yasuhiro Maruoka, Peter L. Choyke, and Hisataka Kobayashi, Interstitial near-infrared photoimmunotherapy: effective treatment areas and light doses needed for use with fiber optic diffusers, Oncotarget 2018 Feb. 16; 9(13), p. 11159-11169
SUMMARY

Technical Problem

Here, as described above, in PDT and NIR-PIT, cancer cells are killed by irradiating cancer cells which have accumulated the complex with light of the excitation wavelength of the photosensitive substance within the complex. On the other hand, in order to reduce the risk of cell damage, it is preferable to avoid light irradiation with respect to normal cells that are not cancer cells. In this respect, in the techniques described in Patent Literature 2 and Patent Literature 3, it is difficult to position the light irradiation site inside the blood vessel. Therefore, it is not possible to selectively irradiate the area where the cancer cells exist.

Such issues are common not only to PDT and NIR-PIT, but to all devices used in examinations or treatments that include the process of light irradiation inside the body. Furthermore, such issues are not limited to devices inserted into a blood vessel, and are common to all devices inserted into a biological lumen, such as the vascular system, lymph gland system, biliary system, urinary tract system, airway system, digestive system, secretory glands, and reproductive organs.

The disclosed embodiments have been made in order to solve at least some of the problems described above. An object of the disclosed embodiments is to provide a light irradiation device and a light irradiation system that are capable of selectively irradiating a specific location in a biological lumen with light.

Solution to Problem

The disclosed embodiments have been made to solve at least some of the problems described above, and can be achieved as the following aspects.

(1) According to an aspect of the disclosed embodiments, a medical light irradiation device is provided. The light irradiation device includes: an elongated main body portion; a light irradiation portion which is provided on one portion of a side surface on a distal end side of a main body portion, and which irradiates light towards outside; and a marker portion which is provided on a distal end side of the main body portion, is radiopaque, and has a shape that enables the location of the light irradiation portion in a circumferential direction to be identified when viewed from an arbitrary direction.

According to this configuration, the light irradiation device is provided with a radiopaque marker portion provided on the distal end side of the main body portion. As a result, a surgeon is capable of determining the insertion direction location of the light irradiation site (light irradiation portion) in a biological lumen by confirming the location of the marker portion inside the body through X-ray imaging. Furthermore, the marker portion is configured so that the location of the light irradiation portion in the circumferential direction can be recognized by the shape of the marker portion when viewed from an arbitrary direction. Therefore, the surgeon can easily position the light irradiation portion in the biological lumen in the circumferential direction in addition to the insertion direction. As a result, the light irradiation device is capable of selectively irradiating a specific location in a biological lumen with light, which enables, for example, the selective irradiation of cancer cells with light in NIR-PIT. In addition, a light irradiation portion that irradiates light to outside is provided on one portion of a side surface on the distal end side of the main body portion. As a result, compared with a configuration in which the light irradiation portion is provided on the entire circumferential direction of the main body portion, the area of the biological tissue which is irradiated with light can be limited. This can contribute to the suppression of biological tissue damage caused by unnecessary light irradiation of biological tissue.

(2) In the light irradiation device according to the above aspect, the marker portion may have a spiral shape extending in an axial direction of the light irradiation device. According to this configuration, the marker portion has a spiral shape extending in an axial direction of the light irradiation device. As a result, by grasping the association between the winding direction of the spiral and the location of the light irradiation portion in advance, the surgeon is capable of easily grasping the irradiation direction of light by the light irradiation portion, even in a state where the light irradiation device has been inserted in a biological lumen. Therefore, the positioning of the light irradiation portion in the circumferential direction can be performed more easily.

(3) In the light irradiation device according to the above aspect, a radiopaque distal end side marker portion may be further provided on a distal end side of the marker portion. According to this configuration, a radiopaque distal end side marker portion is further provided on a distal end side of the marker portion. As a result, the surgeon is capable of easily grasping the location of the distal end side of the marker portion in the biological lumen. Therefore, the positioning of the light irradiation portion in the insertion direction can be performed more easily.

(4) In the light irradiation device according to the above aspect, a radiopaque proximal end side marker portion may be further provided on a proximal end side of the marker portion. According to this configuration, a radiopaque proximal end side marker portion is further provided on a proximal end side of the marker portion. As a result, the surgeon is capable of easily grasping the location of the proximal end side of the marker portion in the biological lumen. Therefore, the positioning of the light irradiation portion in the insertion direction can be performed more easily.

(5) In the light irradiation device according to the above aspect, the main body portion may have an elongated tube shape having an inner cavity, and the marker portion may be embedded in a thick-walled portion constituting a tube wall of the main body portion. According to this configuration, the main body portion has an elongated tube shape having an inner cavity. Therefore, by inserting a guidewire through the inner cavity of the main body portion, the light irradiation device can be easily delivered to a target site in the biological lumen. Furthermore, because the marker portion is embedded in the thick-walled portion constituting the tube wall of the main body portion, the light irradiation device can be made thinner in diameter compared with a case where the marker portion is provided protruding from the main body portion, and damage to the biological tissue caused by the protruding portion can be suppressed.

(6) The light irradiation device according to the above aspect may be further provided with a light conveying portion which is embedded in the thick-walled portion of the main body portion and extends from the distal end side to the proximal end side of the main body portion, and which is connected to a light source on the proximal end side of the main body portion, wherein the light irradiation portion is arranged on a distal end portion of the light conveying portion, and irradiates light transmitted by the light conveying portion to outside. According to this configuration, a light conveying portion which is connected to an external light source and transmits light from the light source to the light irradiation portion is further provided. Consequently, compared with a configuration in which the light source is built into the light irradiation device, the light irradiation device can be made smaller. Furthermore, because the light conveying portion is embedded in the thick-walled portion of the main body portion, the usability of the light irradiation device can be improved compared with a configuration in which the light conveying portion is not embedded.

(7) According to an aspect of the disclosed embodiments, a light irradiation system is provided. The light irradiation system includes: a light irradiation device according to the above aspects; an elongated tube-shaped catheter for inserting the light irradiation device, the catheter having a light transmitting portion provided on at least one portion of a side surface on a distal end side that transmits light inside the tube to outside The disclosed embodiments can be realized in various forms, including a catheter, a light irradiation device, a light irradiation system in which these are separate or integrated, and a manufacturing method of a catheter, a light irradiation device, and a light irradiation system.

BRIEF DESCRIPTION OF DRAWINGS

FIG. 3 is an explanatory diagram illustrating the light irradiation device while in use.

FIG. 7 is an explanatory diagram illustrating a configuration of a light irradiation device according to the fourth embodiment.

FIG. 12 is an explanatory diagram illustrating a configuration of a light irradiation system according to a ninth embodiment.

DETAILED DESCRIPTION OF EMBODIMENTS

First Embodiment

Figure 1:
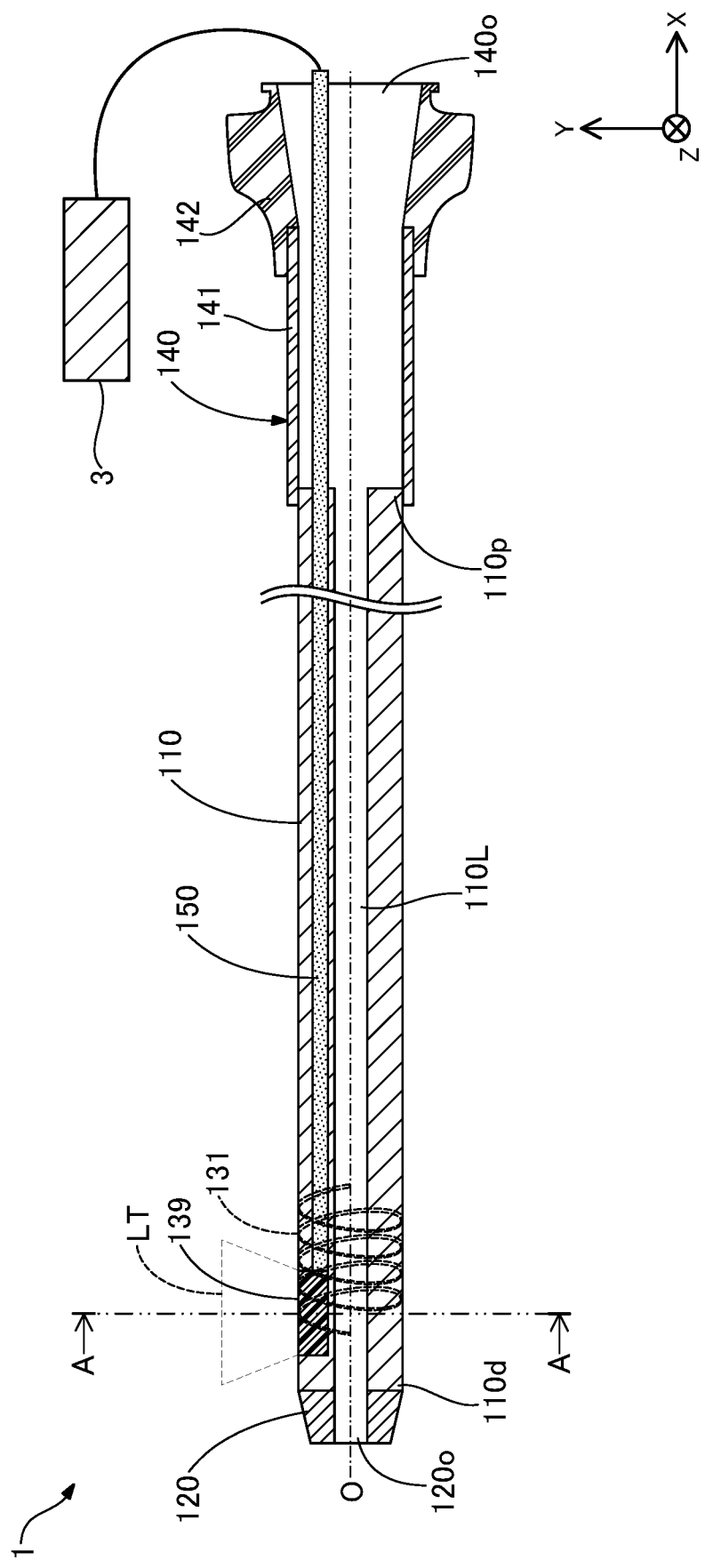
FIG. 1 is an explanatory diagram illustrating a configuration of a light irradiation device according to a first embodiment.

FIG. 1 is an explanatory diagram illustrating a configuration of a light irradiation device 1 according to a first embodiment. The light irradiation device 1 is used by being inserted into a biological lumen, such as the vascular system, lymph gland system, biliary system, urinary tract system, airway system, digestive system, secretory glands, and reproductive organs, and irradiates light from such a lumen of a living body toward living tissue. The light irradiation device 1 can be used, for example, in PDT (Photodynamic Therapy) and NIR-PIT (Near-Infrared Photoimmunotherapy). The following embodiments are illustrated using laser light as an example of light. However, for example, LED light or white light may be used to configure the light irradiation device 1.

In FIG. 1, the axis passing through the center of the light irradiation device 1 is represented by the axis O (dot and dash line). Hereinafter, the axis passing through the center of the light irradiation device 1 and the axis passing through the center of each member (for example, the main body portion 110 and the connector 140) of the light irradiation device 1 will be described as being coincident with the axis O. However, they may be different from each other. In FIG. 1, an X-axis, Y-axis, and Z-axis that are orthogonal to each other are illustrated. The X-axis corresponds to the axial direction of the light irradiation device 1 (the insertion direction of the light irradiation device 1). The Y-axis corresponds to the height direction of the light irradiation device 1. The Z-axis corresponds to the width direction of the light irradiation device 1. The left side (the negative X-axis direction) in FIG. 1 is referred to as the "distal end side" of the light irradiation device 1 and each component. The right side (the positive X-axis direction) in FIG. 1 is referred to as the "proximal end side" of the light irradiation device 1 and each component. Furthermore, in the light irradiation device 1 and each component, the end located on the distal end side is referred to as the "distal end", and the distal end and the vicinity thereof are referred to as the "distal end portion". Further, the end located on the proximal end side is referred to as the "proximal end", and the proximal end and the vicinity thereof are referred to as the "proximal end portion". The distal end side corresponds to the "distal end side" inserted into the living body, and the proximal end side corresponds to the "proximal end side" operated by the surgeon such as a physician. These features are common to the drawings illustrating the overall configurations following FIG. 1.

The light irradiation device 1 has a main body portion 110, a distal tip 120, and a connector 140. The main body portion 110 is an elongated member (shaft) extending along the axis O. The main body portion 110 has a hollow, substantially cylindrical shape with openings at both ends at a distal end portion 110$d$ and a proximal end portion 110$p$. A lumen 110L is provided inside the main body portion 110. The lumen 110L functions as a guidewire lumen for inserting a guidewire into the light irradiation device 1 during delivery of the light irradiation device 1. The outer diameter, the inner diameter, and the length of the main body portion 110 can be arbitrarily determined.

The distal tip 120 is a member which is joined to the distal end portion 110$d$ of the main body portion 110, and travels inside the biological lumen ahead of the other members. As shown in FIG. 1, in order to enable smooth travel of the light irradiation device 1 inside the biological lumen, the distal tip 120 has an outer shape whose diameter is reduced from the proximal end side toward the distal end side. Furthermore, a substantially central portion of the distal tip 120 has a through-hole formed through the distal tip 120 in the axis O direction. The diameter of the through-hole of the distal tip 120 is substantially the same as the diameter of the lumen 110L. An opening 120$o$ of the distal tip 120 is connected to the through-hole, and is used when inserting a guidewire (not illustrated) through the light irradiation device 1. The outer diameter and the length of the distal tip 120 can be arbitrarily determined.

The connector 140 is a member which is arranged on the proximal end side of the light irradiation device 1, and is gripped by the surgeon. The connector 140 includes a connection portion 141 having a substantially cylindrical shape, and a pair of blades 142. The proximal end portion 110$p$ of the main body portion 110 is joined to the distal end portion of the connection portion 141, and the blades 142 are joined to the proximal end portion. The blades 142 may have an integrated structure with the connector 140. The opening 140$o$ of the connector 140 is connected to the lumen 110L via the inside of the connector 140, and is used to withdraw the guidewire that has been inserted into the light irradiation device 1 to outside. The outer diameter, the inner diameter, and the length of the connection portion 141, and the shape of the blades 142 can be arbitrarily determined.

The main body portion 110 of the light irradiation device 1 is further provided with a light conveying portion 150, a light irradiation portion 139, and a marker portion 131. As shown in FIG. 1, the light conveying portion 150 is an optical fiber which is embedded in the thick-walled portion constituting the tube wall of the main body portion 110, and extends along the axis O direction (X-axis direction) from the distal end side to the proximal end side of the main body portion 110. The proximal end portion of the light conveying portion 150 is connected via a connector (not illustrated) to a laser light generator 3 that generates laser light having an arbitrary wavelength, either directly or indirectly via another optical fiber. The laser light generator 3 functions as a "light source" installed outside the light irradiation device 1. The distal end portion of the light conveying portion 150 has the cladding and coating removed from the optical fiber to expose the core.

Figure 2:
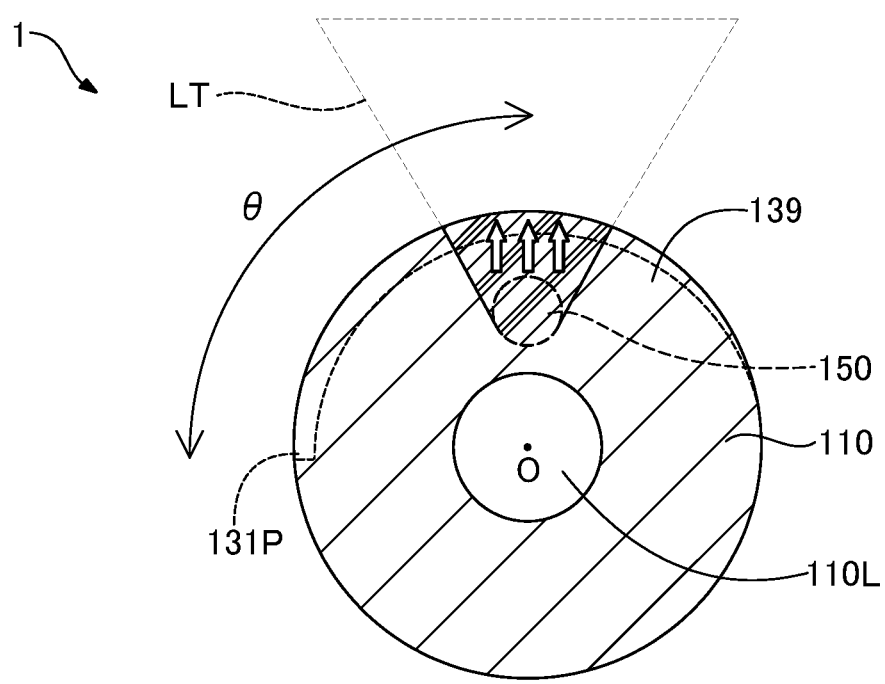
FIG. 2 is an explanatory diagram illustrating a cross-sectional configuration taken along line A-A in FIG. 1.

FIG. 2 is an explanatory diagram illustrating a cross-sectional configuration taken along line A-A in FIG. 1. The light irradiation portion 139 is arranged on the distal end portion of the light conveying portion 150, and irradiates the light transmitted by the light conveying portion 150 to outside of the light irradiation device 1. Specifically, the light conveying portion 150 irradiates an emission light LT from the core exposed at the distal end portion of the light conveying portion 150 to outside in one direction from a side surface of the light irradiation device 1 (FIG. 2: white-filled arrow). As shown in FIG. 2, the light irradiation portion 139 is a resin body covering the distal end of the core of the light conveying portion 150, and is exposed to one portion of the side surface on the distal end side of the main body portion 110. The light irradiation portion 139 can be formed, for example, by applying an acrylic ultraviolet-curable resin containing dispersed fine quartz powder, and curing the resin using ultraviolet light. The light irradiation portion 139 may be realized in other forms, for example, by a light-reflecting mirror instead of a resin body. Furthermore, the light irradiation portion 139 may be formed on one portion of the light conveying portion 150 by applying a known process (such as a process that diagonally cuts the distal end surface, a process that forms a notch, a sandblasting process, or a chemical treatment) to the core exposed at the distal end portion of the light conveying portion 150.

The laser light LT generated by the laser light generator 3 is transmitted from the proximal end side to the distal end side of the light conveying portion 150 via the core of the optical fiber, and is irradiated from the core exposed at the distal end portion through the light irradiation portion 139, and then to outside in one direction from a side surface of the light irradiation device 1 (FIG. 2: white-filled arrow).

The marker portion 131 functions as a marking that represents the location of the light irradiation portion 139. In FIG. 1 and FIG. 2, for convenience of description, the illustration for the marker portion 131 is represented as a schematic view rather than a cross-sectional view (FIGS. 1 and 2: reference numeral 131 displayed as a dashed line). As shown in FIGS. 1 and 2, the marker portion 131 is a member formed by winding a wire in a spiral shape, whose outer diameter is substantially the same as the outer diameter of the main body portion 110. The marker portion 131 is embedded in the thick-walled portion constituting the tube wall of the main body portion 110 on the distal end side of the main body portion 110, and is arranged extending along the thick-walled portion of the main body portion 110 in the axis O direction. Here, in the present embodiment, because the light irradiation portion 139 is provided exposed to one portion of the side surface on the distal end side of the main body portion 110, a portion of the marker portion 131 on the distal end side is embedded in the resin body of the light irradiation portion 139, or is arranged on the surface of the resin body. Furthermore, as shown in FIG. 2, the marker portion 131 is arranged so that the center of the emission light LT from the light irradiation portion 139 is located θ degrees in a right-handed (clockwise) rotation in the circumferential direction from a start-of-winding portion 131P located on the distal end side. In the present embodiment, θ=90 degrees.

The marker portion 131 may be disposed in a different location to the light irradiation portion 139 in the axis O direction (X-axis direction). In other words, the start-of-winding portion 131P may be located on the proximal end side of the proximal end portion of the light irradiation portion 139. Furthermore, the outer diameter of the marker portion 131 can be arbitrarily determined, and may be, for example, larger than the outer diameter of the main body portion 110, an arbitrary size which is at least as large as the inner diameter of the main body portion 110 but smaller than the outer diameter, or smaller than the inner diameter of the main body portion 110 (that is to say, the diameter of the lumen 110L).

The marker portion 131 can be formed of a resin material or a metallic material having radiopacity. For example, when a resin material is used, it can be formed by mixing a radiopaque material such as bismuth trioxide, tungsten, or barium sulfate with a polyamide resin, a polyolefin resin, a polyester resin, a polyurethane resin, a silicon resin, a fluorine resin, or the like. For example, when a metallic material is used, it can be formed of gold, platinum, tungsten, or an alloy containing these elements (such as a platinum-nickel alloy), which are radiopaque materials.

The main body portion 110 preferably has antithrombogenic properties, flexibility, and biocompatibility, and can be formed of a resin material or a metallic material. As the resin material, for example, a polyamide resin, a polyolefin resin, a polyester resin, a polyurethane resin, a silicon resin, or a fluororesin can be used. As the metallic material, for example, stainless steel such as SUS304, a nickel-titanium alloy, a cobalt-chromium alloy, or tungsten steel can be used. Furthermore, the main body portion 110 can also be a bonded structure combining a plurality of the materials mentioned above. The distal tip 120 preferably has flexibility and can be formed of a resin material such as polyurethane, a polyurethane elastomer, or the like. The connector 240 can be formed of a resin material such as polyamide, polypropylene, polycarbonate, polyacetal, polyethersulfone, or the like.

A method of using of the light irradiation device 1 will be described. First, the surgeon inserts a guidewire into the biological lumen. Next, the surgeon inserts the proximal end side of the guidewire through the opening 120o of the distal tip 120 of the light irradiation device 1 shown in FIG. 1 and into the lumen 110L, and pulls it out through the opening 140o of the connector 140. Then, the surgeon pushes the light irradiation device 1 into the biological lumen along the guidewire, and delivers the light irradiation portion 139 of the light irradiation device 1 to the target site of the light irradiation (for example, near the cancer cells in the case of NIR-PIT). As described above, the main body portion 110 of the light irradiation device 1 has an elongated tube shape having the lumen 110L (inner cavity). Therefore, by inserting a guidewire through the lumen 110L of the main body portion 110, the light irradiation device 1 can be easily delivered to the target site in the biological lumen. Note that, during delivery, the surgeon can position the insertion direction (X-axis direction) location of the light irradiation device 1 in the biological lumen while confirming the location of the marker portion 131 in an X-ray image.

FIG. 3 is an explanatory diagram illustrating the light irradiation device 1 while in use. The upper part of FIG. 3 shows the light irradiation device 1 before rotation, and the lower part of FIG. 3 shows the light irradiation device 1 after rotation. In FIG. 3, the guidewire inserted into the lumen 110L is not shown. After positioning the light irradiation device 1 in the insertion direction (X-axis direction), the surgeon confirms the shape of the marker portion 131 in an X-ray image to direct the emission direction of the emission light LT toward the direction of the target site of light irradiation in the biological lumen. Specifically, as shown in the figure, the surgeon can change the emission direction of the emission light LT by rotating the light irradiation device 1 in the circumferential direction (YZ-axis direction) while maintaining the location of the light irradiation device 1 in the X-axis direction. At this time, by grasping the positional relationship between the marker portion 131 and the light irradiation portion 139 described in FIG. 2 in advance, the surgeon can grasp the direction of the emission light LT from the light irradiation portion 139 by the shape of the marker portion 131 in an X-ray image. In this way, the laser light LT transmitted through the light conveying portion 150 and emitted from the light irradiation portion 139 can be emitted toward the external biological tissue.

As described above, according to the light irradiation device 1 of the first embodiment, the light irradiation device 1 is provided with a radiopaque marker portion 131 provided on the distal end side of the main body portion 110. As a result, as described using FIG. 3, the surgeon is capable of determining the insertion direction (X-axis direction) location of the light irradiation site (light irradiation portion 139) in the biological lumen by confirming the location of the marker portion 131 inside the body through X-ray imaging. Furthermore, as a result of having the spiral shape described above, the marker portion 131 is configured so that the circumferential direction (YZ-axis direction) location of the light irradiation portion 139 can be recognized by the shape of the marker portion 131 when viewed from an arbitrary direction outside the body. Therefore, the surgeon can easily position the light irradiation portion 139 in the biological lumen in the circumferential direction in addition to the insertion direction. As a result, according to the light irradiation device 1 of the first embodiment, it is possible to selectively irradiate a specific location in a biological lumen with light, which enables, for example, the selective irradiation of cancer cells with light in NIR-PIT.

Furthermore, the light irradiation portion 139, which irradiates light to outside, is provided on one portion of the side surface on the distal end side of the main body portion 110. As a result, compared with a configuration in which the light irradiation portion 139 is provided on the entire circumferential direction (YZ-axis direction) of the main body portion 110, or in other words, a configuration in which the emission light LT is emitted in the entire circumferential direction of the main body portion 110, the area of the biological tissue which is irradiated with light can be limited. This can contribute to the suppression of biological tissue damage caused by unnecessary light irradiation of biological tissue.

In addition, the marker portion 131 has a spiral shape extending in the axis O direction (X-axis direction) of the light irradiation device 1. As a result, as described in FIG. 3, by grasping the association between the winding direction of the spiral (FIG. 2: right-handed rotation in the circumferential direction) and the location of the light irradiation portion 139 (FIG. 2: a location θ degrees from the start-of-winding portion 131P) in advance, the surgeon is capable of easily grasping the irradiation direction of the emission light LT from the light irradiation portion 139 even in a state where the light irradiation device 1 has been inserted in a biological lumen. Therefore, the positioning of the light irradiation portion 139 in the circumferential direction (YZ-axis direction) can be performed more easily.

In addition, because the marker portion 131 is embedded in the thick-walled portion constituting the tube wall of the main body portion 110, the light irradiation device 1 can be made thinner in diameter compared with a case where the marker portion 131 is provided protruding from the main body portion 110, and damage to the biological tissue caused by the protruding portion can be suppressed. Moreover, the light irradiation device 1 further includes the light conveying portion 150, which is connected to the external laser light generator 3 (light source) and transmits the light from the laser light generator 3 to the light irradiation portion 139. Consequently, compared with a configuration in which the light source is built into the light irradiation device 1, the light irradiation device 1 can be made smaller. Furthermore, because the light conveying portion 150 is embedded in the thick-walled portion of the main body portion 110, the usability of the light irradiation device 1 can be improved compared with a configuration in which the light conveying portion 150 is not embedded.

Second Embodiment

Figure 4:
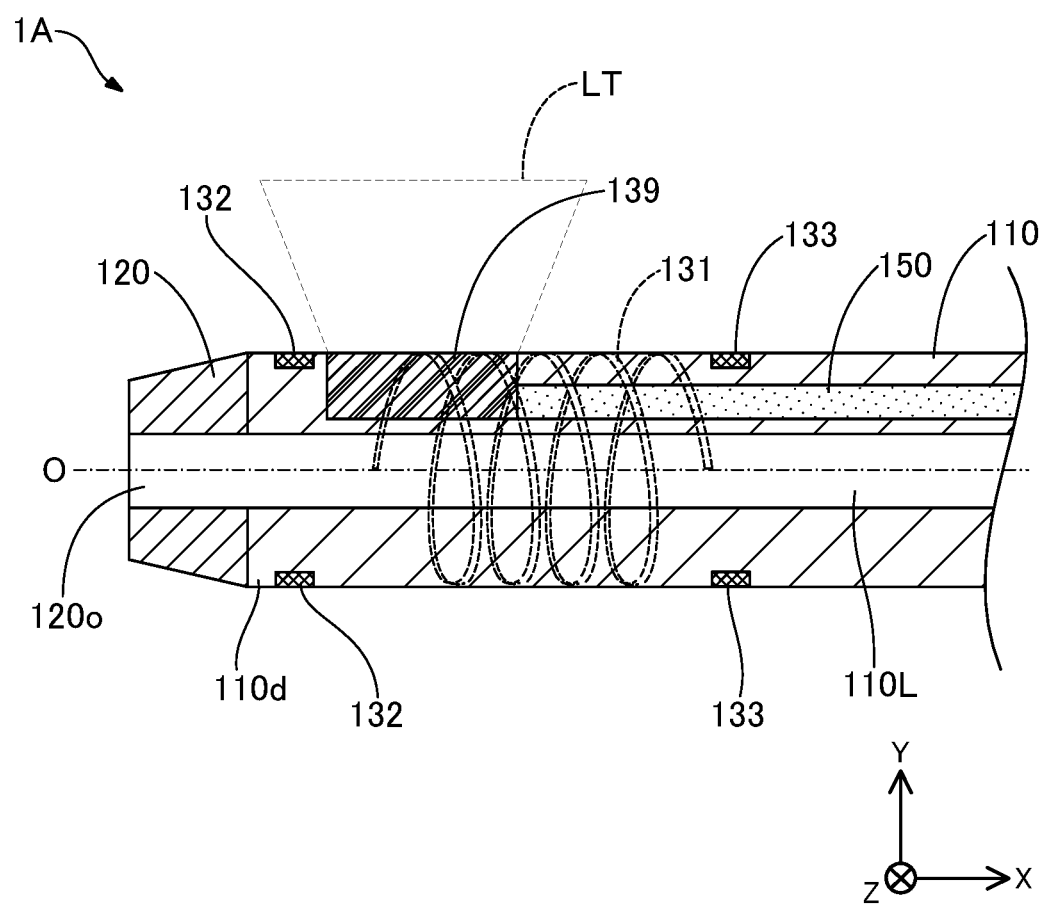
FIG. 4 is an explanatory diagram illustrating a configuration of a light irradiation device according to a second embodiment.

FIG. 4 is an explanatory diagram illustrating a configuration of a light irradiation device 1A according to a second embodiment. The light irradiation device 1A of the second embodiment includes, in addition to the configuration described in the first embodiment, a distal end side marker portion 132 and a proximal end side marker portion 133. The distal end side marker portion 132 is provided on the distal end side of the marker portion 131, and functions as a marking that represents the location of the distal end portion of the marker portion 131. The proximal end side marker portion 133 is provided on the proximal end side of the marker portion 131, and functions as a marking that represents the location of the proximal end of the marker portion 131. In the example of FIG. 4, the distal end side marker portion 132 is provided in close proximity to the distal end portion of the light irradiation portion 139, and the location of the distal end side marker portion 132 and the location of the marker portion 131 do not overlap in the axis O direction (X-axis direction). Similarly, the proximal end side marker portion 133 is provided in close proximity to the proximal end portion of the marker portion 131, and the location of the proximal end side marker portion 133 and the location of the marker portion 131 do not overlap in the axis O direction. However, the locations of the distal end side marker portion 132 and the proximal end side marker portion 133 may overlap with the location of the marker portion 131 in the axis O direction.

The distal end side marker portion 132 and the proximal end side marker portion 133 are both hollow, substantially cylindrically-shaped members. The distal end side marker portion 132 and the proximal end side marker portion 133 are each arranged in a recess formed on the outer surface of the main body portion 110, and are joined to the outer surface of the main body portion 110. In other words, the distal end side marker portion 132 and the proximal end side marker portion 133 are each embedded in the outer surface of the main body portion 110 so as to surround the main body portion 110 in the circumferential direction. The distal end side marker portion 132 and the proximal end side marker portion 133 may also be provided protruding from the outer surface of the main body portion 110 by being joined to the outer surface of a main body portion 110 not having a recess. Like the marker portion 131, the distal end side marker portion 132 and the proximal end side marker portion 133 can be formed of a resin material or a metallic material having radiopacity. The materials of the distal end side marker portion 132 and the proximal end side marker portion 133 may be the same or different from the marker portion 131.

In this way, the light irradiation device 1A may be provided with another marker as a marking that represents the location of the marker portion 131. An effect similar to that of the first embodiment described above can also be exhibited by the light irradiation device 1A according to the second embodiment described above. Furthermore, the light irradiation device 1A of the second embodiment is further provided with the radiopaque distal end side marker portion 132 provided on the distal end side of the marker portion 131. As a result, the surgeon is capable of easily grasping the location of the distal end side of the marker portion 131 in the biological lumen. Therefore, the positioning of the light irradiation portion 139 in the insertion direction can be performed more easily. Also, the radiopaque proximal end side marker portion 133 provided on the proximal end side of the marker portion 131 is provided. As a result, the surgeon is capable of easily grasping the location of the proximal end side of the marker portion 131 in the biological lumen. Therefore, the positioning of the light irradiation portion 139 in the insertion direction can be performed more easily.

Third Embodiment

Figure 5:
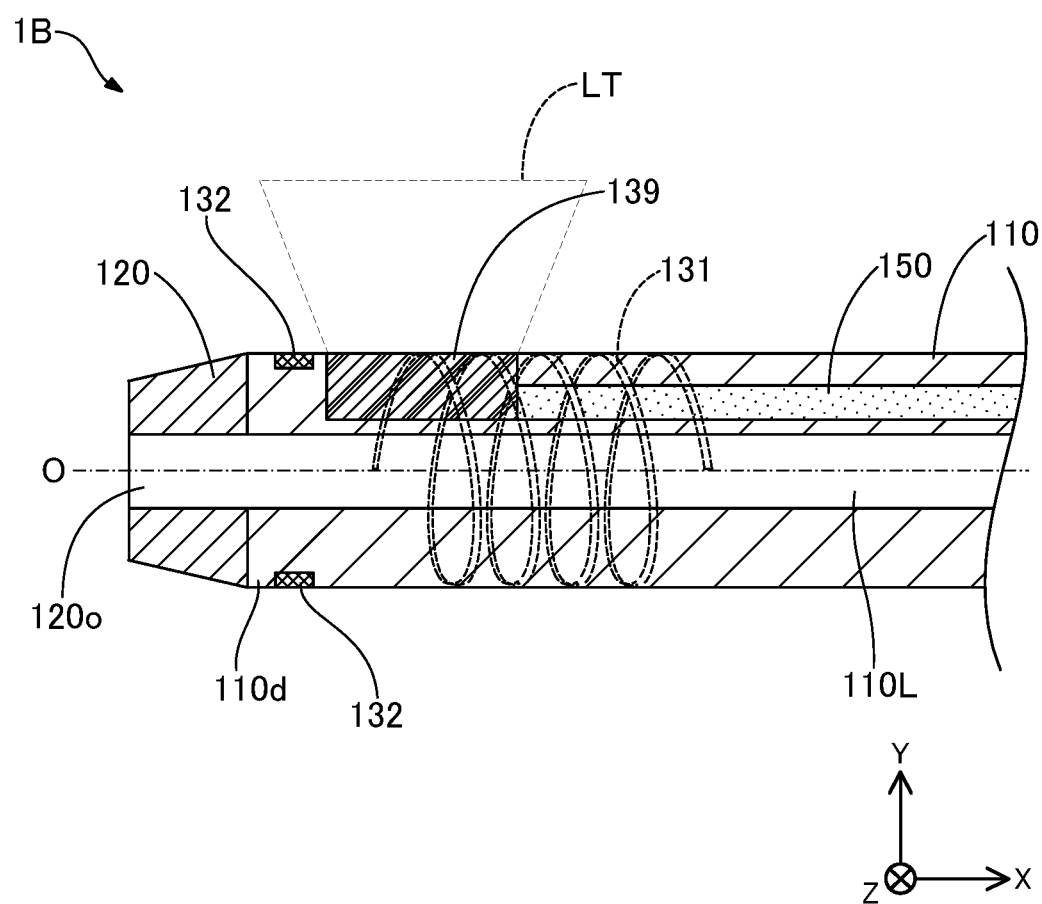
FIG. 5 is an explanatory diagram illustrating a configuration of a light irradiation device according to a third embodiment.

FIG. 5 is an explanatory diagram illustrating a configuration of a light irradiation device 1B according to a third embodiment. The light irradiation device 1B of the third embodiment includes the distal end side marker portion 132 of the configuration described in the second embodiment, but does not include the proximal end side marker portion 133. In this way, the number of other markers provided on the light irradiation device 1B may be one, or may be three or more. An effect similar to that of the first embodiment described above can also be exhibited by the light irradiation device 1B according to the third embodiment described above. Furthermore, the light irradiation device 1B of the third embodiment is further provided with the radiopaque distal end side marker portion 132 provided on the distal end side of the marker portion 131. As a result, the surgeon is capable of easily grasping the location of the distal end side of the marker portion 131 in the biological lumen. Therefore, the positioning of the light irradiation portion 139 in the insertion direction can be performed more easily.

Fourth Embodiment

Figure 6:
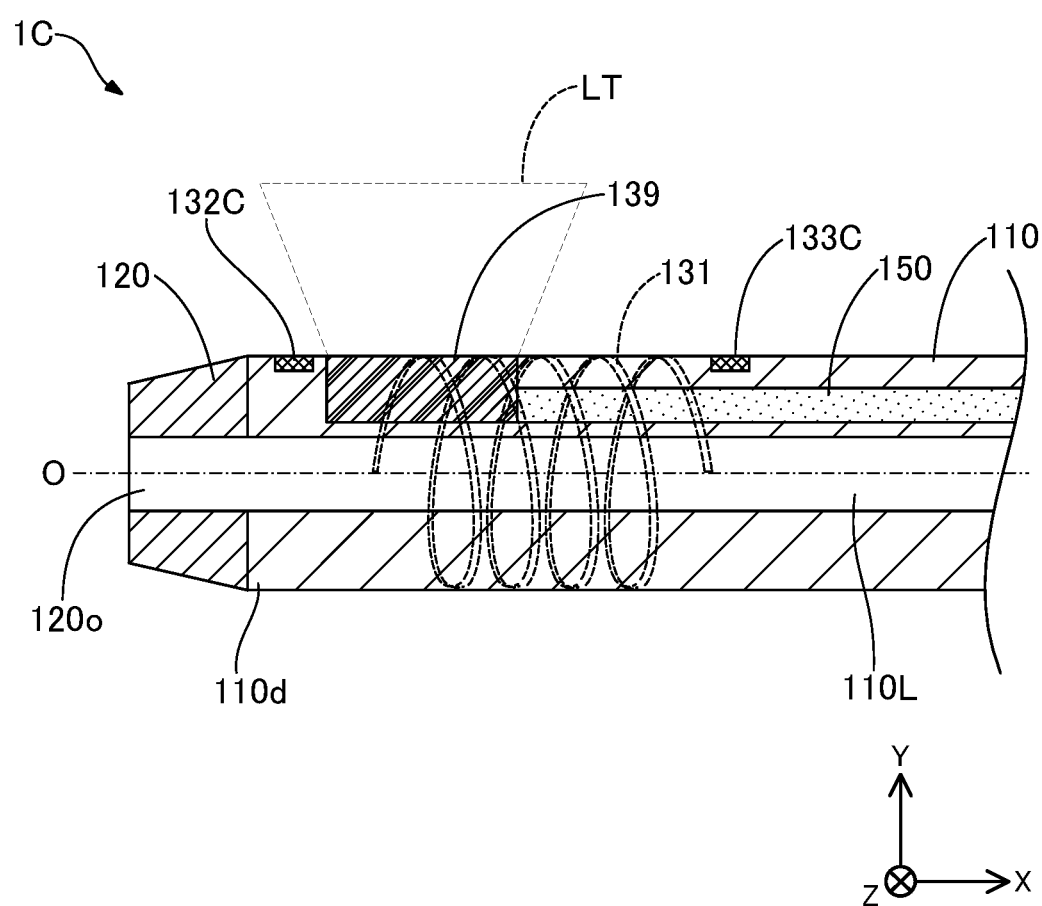
FIG. 6 is an explanatory diagram illustrating a configuration of a light irradiation device according to a fourth embodiment.

FIG. 6 and FIG. 7 are explanatory diagrams illustrating a configuration of a light irradiation device 1C according to a fourth embodiment. FIG. 7(A) shows an example of the configuration of the light irradiation device 1C viewed from the positive Y-axis direction. FIG. 7(B) shows another example of the configuration of the light irradiation device 1C viewed from the positive Y-axis direction. The light irradiation device 1C includes a distal end side marker portion 132C instead of the distal end side marker portion 132 described in the second embodiment, and includes a proximal end side marker portion 133C instead of the proximal end side marker portion 133. The distal end side marker portion 132 and the proximal end side marker portion 133 are each provided on one portion of the circumferential direction (YZ-axis direction) of the light irradiation device 1C. In the example of FIG. 7(A), the distal end side marker portion 132C is provided along the side of the light irradiation portion 139 on the distal end side, and in substantially the same area as the light irradiation portion 139. Similarly, the proximal end side marker portion 133C is provided in a location leaving a predetermined spacing with the side of the light irradiation portion 139 on the proximal end side, and in substantially the same area as the light irradiation portion 139. In the example of FIG. 7(B), the distal end side marker portion 132C and the proximal end side marker portion 133C are provided so as to surround the light irradiation portion 139.

In this way, various configurations can be adopted for the distal end side marker portion 132C and the proximal end side marker portion 133C, and they may be provided only in one portion of the circumferential direction as shown in the drawing. An effect similar to that of the first and second embodiments described above can also be exhibited by the light irradiation device 1C according to the fourth embodiment described above. Furthermore, in the light irradiation device 1C of the fourth embodiment, compared with a configuration in which the distal end side marker portion 132C and the proximal end side marker portion 133C are provided on the entire circumferential direction, the distinction with the spiral-shaped marker portion 131 can be made more easily, and the production cost of the light irradiation device 1C can be reduced.

Fifth Embodiment

Figure 8:
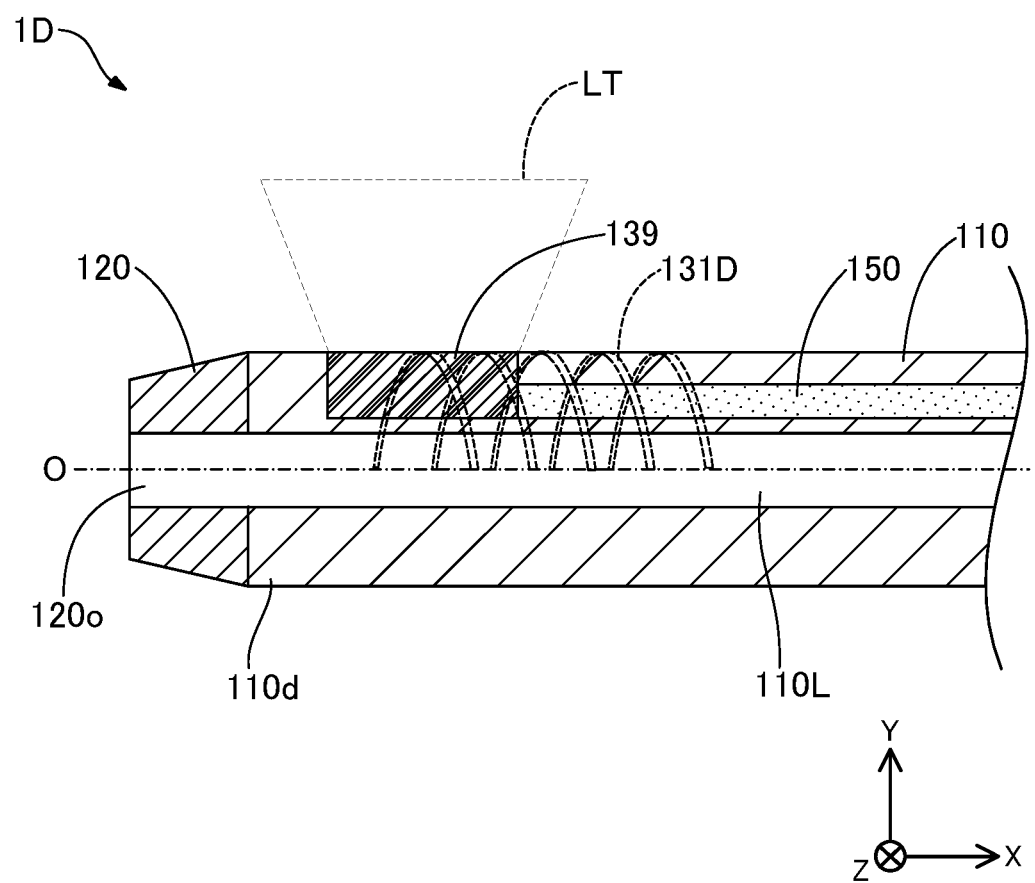
FIG. 8 is an explanatory diagram illustrating a configuration of a light irradiation device according to a fifth embodiment.

FIG. 8 is an explanatory diagram illustrating a configuration of a light irradiation device 1D according to a fifth embodiment. The light irradiation device 1D of the fifth embodiment includes, in the configuration described in the first embodiment, a marker portion 131D instead of the marker portion 131. The marker portion 131D includes a plurality of members made by bending wires into a semicircular arc shape. Each of the members is arranged so as to extend in the thick-walled portion of the main body portion 110 in the axis O direction (X-axis direction) by being embedded at substantially equal intervals in the axis O direction (X-axis direction) on the distal end side of the main body portion 110, and in the thick-walled portion constituting the tube wall of the main body portion 110 and the light irradiation portion 139. Like the marker portion 131, the marker portion 131D can be formed of a resin material or a metallic material having radiopacity. The material of the marker portion 131D may be the same or different from the marker portion 131. As a result of including such a marker portion 131D, in the light irradiation device 1D, it is possible to recognize the location of the light irradiation portion 139 in the circumferential direction (YZ-axis direction) by the shape of the marker portion 131D when viewed from an arbitrary direction outside the body.

In this way, various shapes and configurations can be adopted for the marker portion 131D. As shown in the drawing, it may be configured by a plurality of members made by bending wires into a semicircular arc shape. Furthermore, each member is not limited to a semicircular arc shape, and a circular arc of an arbitrary angle (for example, a letter-C shape), a shape that imitates one portion of a polygon, and the like can be adopted. An effect similar to that of the first embodiment described above can also be exhibited by the light irradiation device 1D according to the fifth embodiment described above.

Sixth Embodiment

Figure 9:
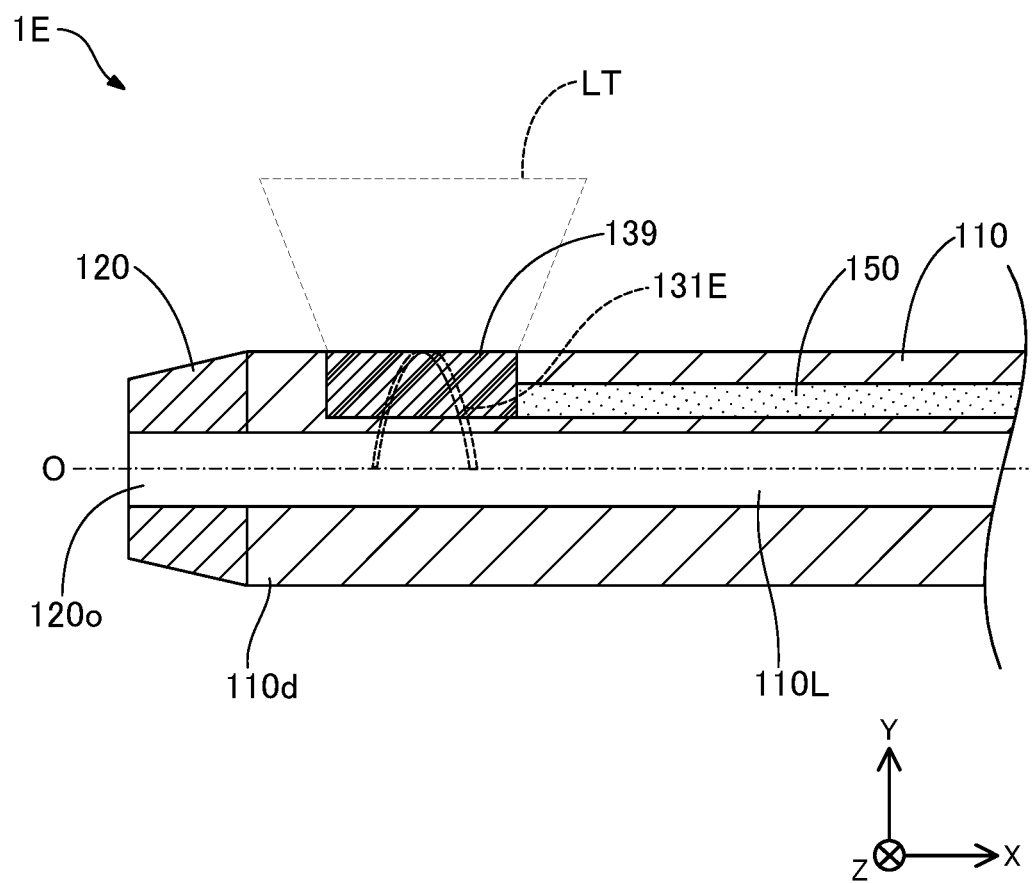
FIG. 9 is an explanatory diagram illustrating a configuration of a light irradiation device according to a sixth embodiment.

FIG. 9 is an explanatory diagram illustrating a configuration of a light irradiation device 1E according to a sixth embodiment. The light irradiation device 1E of the sixth embodiment includes, in the configuration described in the first embodiment, a marker portion 131E instead of the marker portion 131. The marker portion 131E includes a single member made by bending a wire into a semicircular arc shape. This member is embedded on the distal end side of the main body portion 110, and in the thick-walled portion constituting the tube wall of the main body portion 110 and the light irradiation portion 139. Like the marker portion 131, the marker portion 131E can be formed of a resin material or a metallic material having radiopacity. The material of the marker portion 131E may be the same or different from the marker portion 131. As a result of including such a marker portion 131E, in the light irradiation device 1E, it is possible to recognize the location of the light irradiation portion 139 in the circumferential direction (YZ-axis direction) by the shape of the marker portion 131E when viewed from an arbitrary direction outside the body.

In this way, various shapes and configurations can be adopted for the marker portion 131E. As shown in the drawing, it may be configured by a single member made by bending a wire into a semicircular arc shape. Furthermore, each member is not limited to a semicircular arc shape, and a circular arc of an arbitrary angle (for example, a letter-C shape), a shape that imitates one portion of a polygon, and the like can be adopted. An effect similar to that of the first embodiment described above can also be exhibited by the light irradiation device 1E according to the sixth embodiment described above.

Seventh Embodiment

Figure 10:
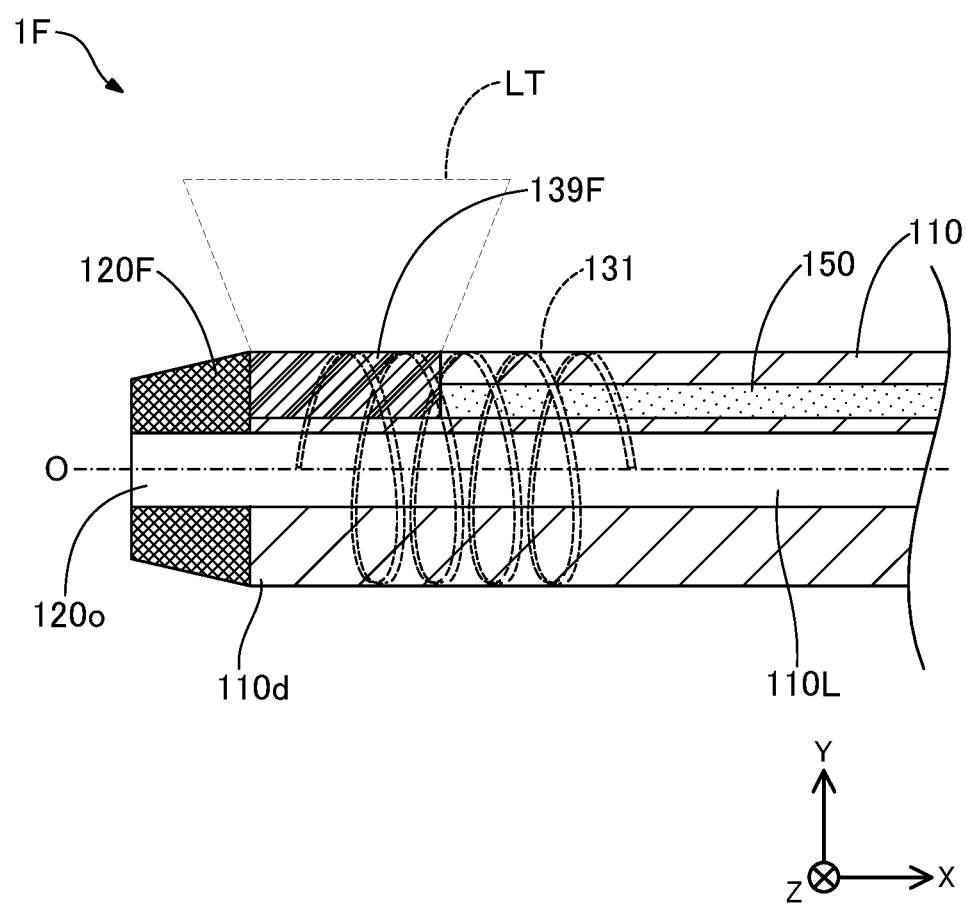
FIG. 10 is an explanatory diagram illustrating a configuration of a light irradiation device according to a seventh embodiment.

FIG. 10 is an explanatory diagram illustrating a configuration of a light irradiation device 1F according to a seventh embodiment. The light irradiation device 1F of the seventh embodiment includes, in the configuration described in the first embodiment, a light irradiation portion 139F instead of the light irradiation portion 139, and a distal tip 120F instead of the distal tip 120. The light irradiation portion 139F is provided exposed on one portion of a side surface of the distal end portion 110D of the main body portion 110. The distal tip 120F is joined to the distal end portion of the light irradiation portion 139F, and the distal end portion 110d of the main body portion 110. The distal tip 120F is formed of a resin material or a metallic material having radiopacity, and functions as a marking representing the location of the distal end portion of the marker portion 131. The material of the distal tip 120F may be the same or different from the marker portion 131.

In this way, various configurations can be adopted for the light irradiation device 1F. The distal tip 120F may function as the distal end side marker portion 132 (second embodiment) by forming the distal tip 120F with a resin material or a metallic material having radiopacity. An effect similar to that of the first, second and third embodiments described above can also be exhibited by the light irradiation device 1F according to the seventh embodiment described above. Furthermore, in the light irradiation device 1F of the seventh embodiment, the distal tip 120F can be made to function as the distal end side marker portion 132. Therefore, the production process of the light irradiation device 1F can be simplified compared with a case where a separate distal end side marker portion 132 is provided.

Eighth Embodiment

Figure 11:
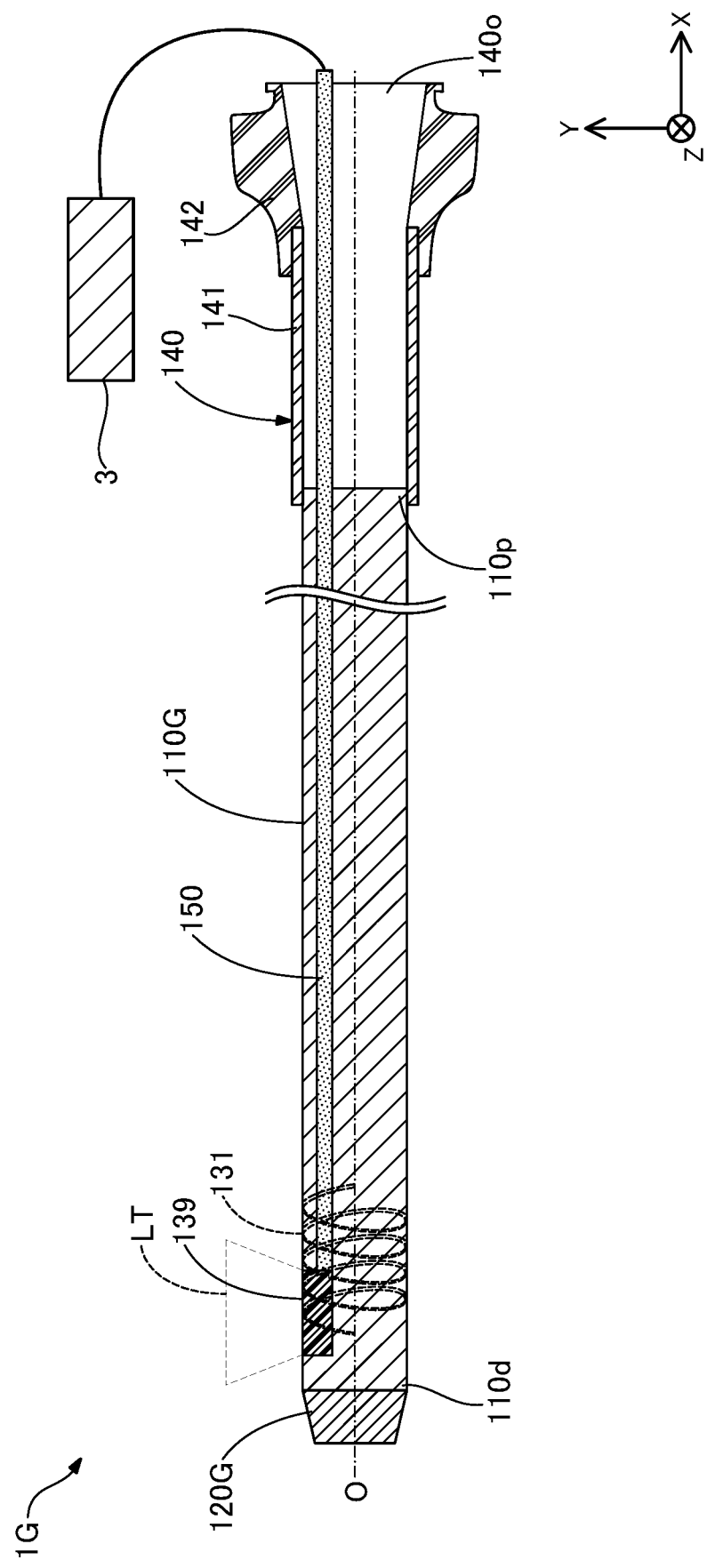
FIG. 11 is an explanatory diagram illustrating a configuration of a light irradiation device according to an eighth embodiment.

FIG. 11 is an explanatory diagram illustrating a configuration of a light irradiation device 1G according to an eighth embodiment. The light irradiation device 1G of the eighth embodiment includes, in the configuration described in the first embodiment, a main body portion 110G instead of the main body portion 110, and a distal tip 120G instead of the distal tip 120. The inside of the main body portion 110G is not provided with the lumen 110L (first embodiment). Furthermore, a through-hole is not formed in the distal tip 120G. In this way, various configurations can be adopted for the light irradiation device 1G. For example, a configuration is possible in which a guidewire lumen as illustrated above is not provided. An effect similar to that of the first embodiment described above can also be exhibited by the light irradiation device 1G according to the eighth embodiment described above.

Ninth Embodiment

FIG. 12 is an explanatory diagram illustrating a configuration of a light irradiation system according to a ninth embodiment. The light irradiation system of the ninth embodiment includes, in addition to the light irradiation device 1 described in the first embodiment, a catheter 2 for inserting the light irradiation device 1. The catheter 2 has an elongated tube shape, and includes a main body portion 210, a distal tip 220, and a connector 240. The main body portion 210 is an elongated member extending along the axis O, and has a hollow, substantially cylindrical shape with openings at both ends at a distal end portion 210d and a proximal end portion 210p. A lumen 210L is provided inside the main body portion 210. The diameter phi 2 of the lumen 210L is larger than the outer diameter phi 4 of the light irradiation device 1 (phi 2>phi 4). The lumen 210L functions as a guidewire lumen for inserting a guidewire into the catheter 2 during delivery of the catheter 2. After delivery of the catheter 2, the lumen 210L functions as a device lumen for inserting the light irradiation device 1 into the catheter 2.

The distal tip 220 is a member which is joined to the distal end portion 210d of the main body portion 210, and travels inside the biological lumen ahead of the other members. In order to enable smooth travel of the catheter 2 inside the biological lumen, the distal tip 220 has an outer shape whose diameter is reduced from the proximal end side toward the distal end side. A substantially central portion of the distal tip 220 has a through-hole formed through the distal tip 220 in the axis O direction. Here, the diameter phi 1 of the through-hole is smaller than the diameter phi 2 of the lumen 210L of the main body portion 210. For this reason, at the boundary between the main body portion 210 and the distal tip 220, a step is formed due to the protrusion of the inner surface 220i of the distal tip 220. The opening 220o of the distal tip 220 is connected to the through-hole, and is used when inserting a guidewire (not illustrated) through the catheter 2. The outer diameter and the length of the distal tip 220 can be arbitrarily determined.

The connector 240 is a member which is arranged on the proximal end side of the catheter 2, and is gripped by the surgeon. The connector 240 includes a connection portion 241 having a substantially cylindrical shape, and a pair of blade portions 242. The proximal end portion 210$p$ of the main body portion 210 is joined to the distal end portion of the connection portion 241, and the blade portions 242 are joined with the proximal end portion. The blade portions 242 may have a structure in which they are integrated with the connector 240. The opening 240$o$ of the connector 240 is connected to the lumen 210L via the inside of the connector 240, and is used when inserting the light irradiation device 1 into the catheter 2. The outer diameter, the inner diameter, and the length of the connection portion 241, and the shape of the blade portions 242 can be arbitrarily determined.

The main body portion 210 of the catheter 2 is further provided with a light transmitting portion 239, a distal end side marker portion 231, and a proximal end side marker portion 232. The light transmitting portion 239 transmits the light inside the main body portion 210 to outside. The light transmitting portion 239 is member having a hollow, substantially cylindrical shape. It has substantially the same outer diameter as the outer diameter of the main body portion 210, and substantially the same inner diameter as the diameter phi 2 of the lumen 210L of the main body portion 210. In other words, the light transmitting portion 239 is provided on the entire circumferential direction (YZ-axis direction), and transmits the light inside the main body portion 210 to outside in the entire circumferential direction. The light transmitting portion 239 is joined to the main body portion 210 on both the proximal end side and the distal end side. The light transmitting portion 239 can be formed from a transparent resin material having light transmitting properties, such as an acrylic resin, polyethylene terephthalate, polyvinyl chloride, and the like.

The distal end side marker portion 231 and the proximal end side marker portion 232 function as markings representing the location of the light transmitting portion 239. The distal end side marker portion 231 is provided in close proximity to the distal end portion of the light transmitting portion 239, and functions as a marking that represents the location of the distal end portion of the light transmitting portion 239. The proximal end side marker portion 232 is provided in close proximity to the proximal end portion of the light transmitting portion 239, and functions as a marking that represents the location of the proximal end portion of the light transmitting portion 239. The distal end side marker portion 231 and the proximal end side marker portion 232 are both hollow, substantially cylindrically-shaped members. The distal end side marker portion 231 and the proximal end side marker portion 232 are each arranged in a recess formed on the outer surface of the main body portion 210, and are joined to the outer surface of the main body portion 210. In other words, the distal end side marker portion 231 and the proximal end side marker portion 232 are each embedded in the outer surface of the main body portion 210 so as to surround the main body portion 210 in the circumferential direction. The distal end side marker portion 231 and the proximal end side marker portion 232 may also be provided protruding from the outer surface of the main body portion 210 by being joined to the outer surface of the main body portion 210 not having a recess.

Like the marker portion 131 of the light irradiation device 1, the distal end side marker portion 231 and the proximal end side marker portion 232 can be formed of a resin material or a metallic material having radiopacity. Like the main body portion 110 of the light irradiation device 1, the main body portion 210 can be formed of a resin material or a metallic material. Like the distal tip 120 of the light irradiation device 1, the distal tip 220 can be formed of a resin material having flexibility. Like the connector 140 of the light irradiation device 1, the connector 240 can be formed of a resin material.

The method of using the light irradiation system of the ninth embodiment will be described. First, the surgeon inserts a guidewire into the biological lumen. Next, the surgeon inserts the proximal end side of the guidewire through the opening 220$o$ of the distal tip 220 of the catheter 2 shown in FIG. 12 and into the lumen 210L, and causes it to protrude from the opening 240$o$ of the connector 240. Then, the surgeon pushes the catheter 2 into the biological lumen along the guidewire, and delivers the light transmitting portion 239 of the catheter 2 to the target site of the light irradiation (for example, near the cancer cells in the case of NIR-PIT). In this way, by inserting a guidewire through the through-hole formed in the distal tip 220 of the catheter 2, the surgeon can easily deliver the catheter 2 to the target site in the biological lumen. Note that, during delivery, the surgeon can position the catheter 2 in the biological lumen while confirming the locations of the distal end side marker portion 231 and the proximal end side marker portion 232 arranged in close proximity to the light transmitting portion 239 in an X-ray image. Then, the surgeon then removes the guidewire from the catheter 2.

Next, the surgeon inserts the light irradiation device 1 through the opening 240$o$ of the connector 240 of the catheter 2. The surgeon pushes the light irradiation device 1 along the lumen 210L of the catheter 2 toward the distal end side of the catheter 2. Here, as long as the diameter phi 1 of the through-hole of the distal tip 220 of the catheter 2 is made smaller than the diameter phi 3 of the distal end surface 120$e$ of the distal tip 120 of the light irradiation device 1 (phi 1<phi 3), the distal end surface 120$e$ of the light irradiation device 1 collides with the inner surface 220$i$ of the distal tip 220 when the light irradiation device 1 is inserted into the catheter 2, and the light irradiation device 1 can be prevented from going through to the distal end side.

Then, the surgeon positions the light irradiation portion 139 and the light transmitting portion 239 in the axis O direction (X-axis direction) by confirming the positional relationship between the marker portion 131 of the light irradiation device 1 and the distal end side marker portion 231 and the proximal end side marker portion 232 of the catheter 2 in an X-ray image. After positioning the light irradiation portion 139 and the light transmitting portion 239 in the axis O direction, the surgeon positions the light irradiation portion 139 in the circumferential direction (in the YZ-axis direction) by the method described in the first embodiment, and irradiates the target site in the biological lumen with light. Note that, it is not necessary to remove the guidewire after positioning the catheter 2 by the biological lumen (before inserting the light irradiation device 1 into the catheter 2). In this case, as described in the first embodiment, the guidewire is inserted into the lumen 110L of the light irradiation device 1, and the light irradiation device 1 may be delivered in a state where the light irradiation device 1 inserted into the catheter 2.

In this way, the light irradiation device 1 may be used in combination with the catheter 2 provided with the light transmitting portion 239 that transmits light from the light irradiation device 1 to outside. Further, the configuration of the catheter 2 described above is only an example, and various modifications are possible. An effect similar to that of the first embodiment described above can also be exhibited by the light irradiation system according to the ninth embodiment described above. In addition, according to the light irradiation system of the ninth embodiment, the range of procedures can be expanded by using the light irradiation device 1 in combination with the catheter 2.

Tenth Embodiment

Figure 13:
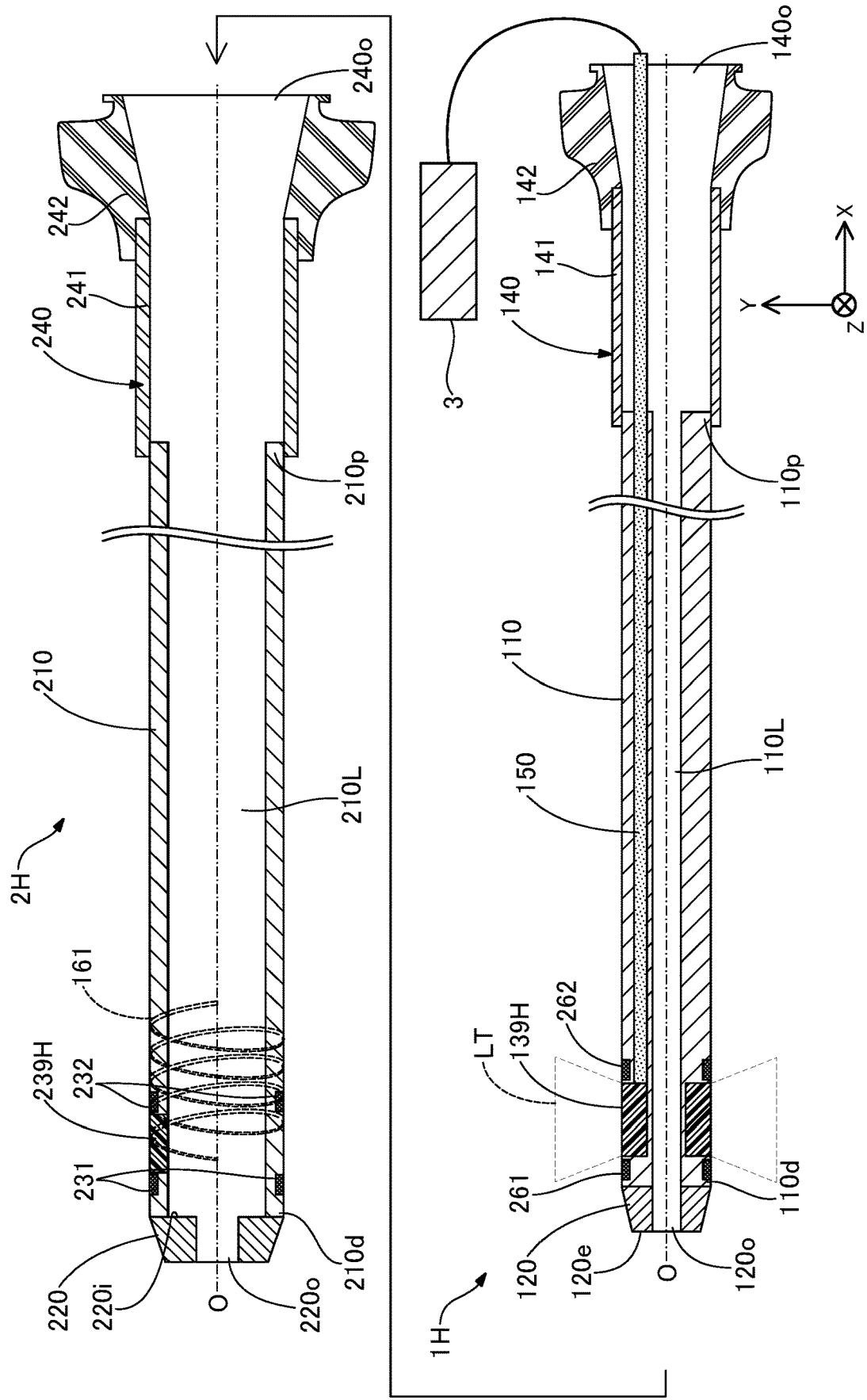
FIG. 13 is an explanatory diagram illustrating a configuration of a light irradiation system according to a tenth embodiment.

FIG. 13 is an explanatory diagram illustrating a configuration of a light irradiation system according to a tenth embodiment. The light irradiation system of the tenth embodiment includes a light irradiation device 1H instead of the light irradiation device 1 described in the first embodiment, and a catheter 2H instead of the catheter 2 described in the ninth embodiment.

The light irradiation device 1H has a distal end side marker portion 261 and a proximal end side marker portion 262 instead of the marker portion 131, and a light irradiation portion 139H instead of the light irradiation portion 139. The distal end side marker portion 261 is provided in close proximity to the distal end portion of the light irradiation portion 139, and functions as a marking that represents the location of the distal end portion of the light irradiation portion 139. The proximal end side marker portion 262 is provided in close proximity to the proximal end portion of the light irradiation portion 139, and functions as a marking that represents the location of the proximal end portion of the light irradiation portion 139. The configurations of the distal end side marker portion 261 and the proximal end side marker portion 262 are the same as those of the distal end side marker portion 231 and the proximal end side marker portion 232 of the catheter 2 described in the ninth embodiment. At least one of the distal end side marker portion 261 and the proximal end side marker portion 262 may be omitted. The light irradiation portion 139H is a solid, substantially cylindrical member having substantially the same diameter as the outer diameter of the main body portion 110. The light irradiation portion 139H is joined to the main body portion 110 on the proximal end side and the distal end side. Furthermore, the surface on the proximal end side of the light irradiation portion 139H covers the distal end of the exposed core of the light conveying portion 150. As a result, in the light irradiation device 1H, the laser light LT generated by the laser light generator 3 is irradiated through the light irradiation portion 139H, and then to outside from the entire circumferential direction of the light irradiation device 1H.

The catheter 2H further includes a marker portion 161, and a light transmitting portion 239H instead of the light transmitting portion 239. The marker portion 161 functions as a mark that represents the location of the light transmitting portion 239. The configuration of the marker portion 161 is the same as that of the marker portion 131 of the light irradiation device 1 described in the first embodiment. The light transmitting portion 239H is an arc-shaped plate member and is joined to the body portion 210 by being fitted to one portion of the main body portion 210. As a result, in the catheter 2H, the light transmitting portion 239H is provided in one portion of the circumferential direction, and transmits the light inside the main body portion 110 to outside in one portion of the circumferential direction.

When the light irradiation system of the tenth embodiment is used, the surgeon uses the catheter 2H to position the insertion direction (X-axis direction) and to position the circumferential direction (YZ-axis direction) in advance. Then, the surgeon inserts the light irradiation device 1H into the catheter 2H, and positions the light irradiation device 1H in the insertion direction (X-axis direction) inside the catheter 2H. Then, the laser light LT is emitted. As described above, the catheter 2H may be provided with a marker portion 161 that enables, due to the shape when viewed from an arbitrary direction, the circumferential direction location of the light irradiation portion 139 to be recognized after being inserted into the catheter 2H. Furthermore, the light irradiation portion 139H and the light transmitting portion 239H can be provided in an arbitrary area in the circumferential direction, and as shown in FIG. 13, the light irradiation system may be configured by combining a light transmitting portion 239H that transmits light to a portion of the circumferential direction, and a light irradiation portion 139H that irradiates light to the entire circumference. Moreover, a light irradiation portion 139 (FIG. 12) that irradiates light to a portion of the circumferential direction, and a light transmitting portion 239H (FIG. 13) that transmits light to a portion of the circumferential direction may be combined. Also, a light irradiation portion 139H (FIG. 13) that irradiates light to the entire circumference, and a light transmitting portion 239 (FIG. 12) that transmits light to the entire circumference may be combined. An effect similar to that of the first embodiment described above can also be exhibited by the light irradiation system according to the tenth embodiment described above.

Eleventh Embodiment

Figure 14:
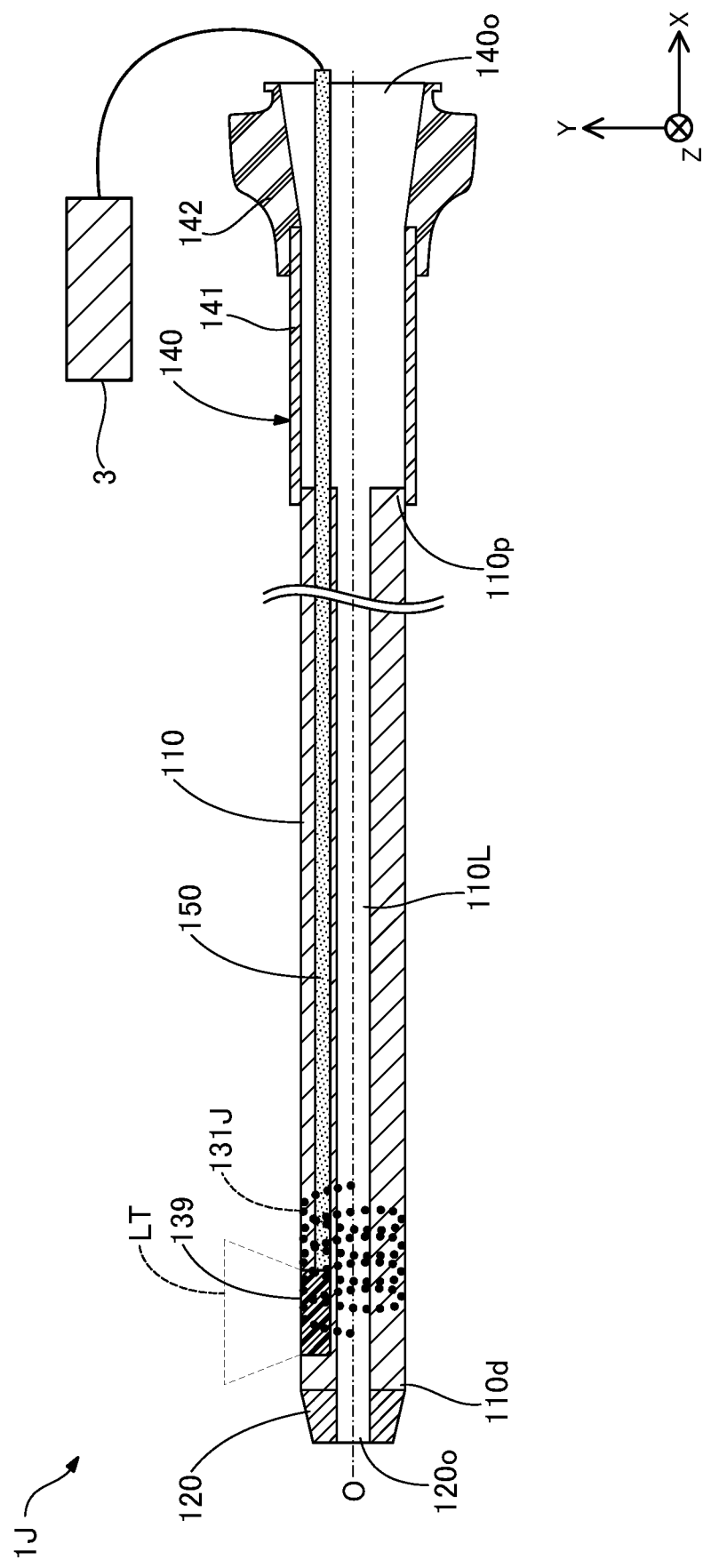
FIG. 14 is an explanatory diagram illustrating a configuration of a light irradiation device according to an eleventh embodiment.

FIG. 14 is an explanatory diagram illustrating a configuration of a light irradiation device 1J according to an eleventh embodiment. The light irradiation device 1J is provided with a marker portion 131J instead of the marker portion 131 of the first embodiment. The marker portion 131J is composed of radiopaque granular material arranged in a spiral shape. In this way, the marker portion 131J can be arbitrarily changed to the extent that the circumferential direction (YZ-axis direction) location of the light irradiation portion 139 can be recognized by the shape of the marker portion 131J when viewed from an arbitrary direction. For example, it may be made of a granular body instead of a wire, or it may be made by mixing a powder having radiopacity with the resin material of the main body portion 110. An effect similar to that of the first embodiment described above can also be exhibited by the light irradiation device 1J according to the eleventh embodiment described above.

MODIFICATION EXAMPLES OF THE EMBODIMENTS

The disclosed embodiments are not limited to the above-described embodiments, and may be implemented in various modes without departing from the spirit of the disclosed embodiments. For example, the following modifications are also possible.

Modification Example 1

In the first to ninth embodiments above, examples of the configuration of the light irradiation devices 1, 1A to 1G, and the catheter 2 have been described. However, the configuration of the light irradiation device 1 and the catheter 2 can be modified in various ways. For example, a reinforcing layer composed of a braided body or a coil body may be embedded in the main body portion 110 of the light irradiation device 1 and the main body portion 210 of the catheter 2. In this way, the torquability and the shape retention of the light irradiation device 1 and the catheter 2 can be improved. For example, a coating consisting of a hydrophilic or hydrophobic resin may be applied to the outer surface of the light irradiation device 1 or to the outer surface of the catheter 2. In this way, the slidability of the light irradiation device 1 and the catheter 2 in the biological lumen can be improved. An antithrombotic material such as heparin may be coated on the outer surface of the light irradiation device 1 or on the outer surface of the catheter 2. In this way, it is possible to suppress a decrease in laser output due to adhesion of a blood clot to the inner or outer surface of the catheter 2 or the outer surface of the light irradiation device 1 caused by irradiation of the emission light (laser light) LT.

For example, the catheter 2 may be provided with an expansion portion that can be expanded in the radial direction (YZ direction). For example, a balloon made of a flexible thin film or a mesh body in which wires have been processed into a mesh shape can be used as the expansion portion. The expansion portion can be provided in the main body portion 210 on at least one of the distal end side of the light transmitting portion 239 and the proximal end side of the light transmitting portion 239. In this way, after positioning the catheter 2 in the biological lumen, the catheter 2 can be fixed in the biological lumen by expanding the expansion portion. Furthermore, if a balloon is used as the expansion portion, the blood flow at the light-irradiated position can be blocked. Therefore, light can be prevented from being blocked by the blood flow.

For example, the light irradiation device 1 may be configured as a multi-lumen catheter having a separate lumen that is different from the lumen 110L through which the light conveying portion 150 is inserted. Similarly, the catheter 2 may be configured as a multi-lumen catheter having a plurality of lumens that are different from the lumen 210L.

For example, an inner surface 220i of the distal tip 220 of the catheter 2 and an outer surface 120e of the distal tip 120 of the light irradiation device 1 may be made of a magnetic body, and configured to attract each other. In this way, a state where the light irradiation device 1 is inserted into the catheter 2, and the distal tip 120 is pressed against the distal tip 220 can be easily maintained.

For example, at least one of the light irradiation device 1 and the catheter 2 may further include a temperature sensor. The temperature sensor can be configured by, for example, a pair of thermocouples embedded in the thick-walled portion of the main body portion 110 or the main body portion 210, and measure the temperature of the biological tissue in close proximity to the light irradiation portion 139 or the light transmitting portion 239. In this way, temperature changes of the biological tissue caused by light irradiation can be observed in real time, which can contribute to the suppression of blood coagulation and damage to biological tissue caused by light irradiation.

Modification Example 2

In the first to eleventh embodiments above, examples of the configuration of the marker portions 131, 131D, 131E, and 131J have been described. Furthermore, various changes can be made to the configuration of the marker portions 131, 131D, 131E, and 131J to the extent that the circumferential direction location of the light irradiation portion 139 can be recognized by the shape of the marker portion 131 when viewed from an arbitrary direction. For example, the marker portion 131 may be configured to have a wave shape extending along the axis O direction, or a zigzag shape extending along the axis O direction on the surface of the main body portion 110.

Modification Example 3

In the first to eleventh embodiments above, examples of the configuration of the light irradiation portion 139 and the light transmitting portion 239 have been described. However, the configuration of the light irradiation portion 139 and the light transmitting portion 239 can be modified in various ways. For example, by configuring the light irradiation portion 139 with a radiopaque material, the light irradiation portion 139 and the distal end side marker portion 132 may be integrally configured. Similarly, by configuring the light transmitting portion 239 with a radiopaque material, the light transmitting portion 239, the distal end side marker portion 231 and the proximal end side marker portion 232 may be integrally configured.

For example, at least one of the light irradiation portion 139 and the light transmitting portion 239 may be formed as a notch (a through-hole communicating the lumen and outside) formed in the main body portion 110 or the main body portion 210. In this way, the light irradiation portion 139 and the light transmitting portion 239 can be easily configured.

For example, the distal end surface of the light conveying portion 150 may be diagonally cut, and the distal end surface may be configured as the light irradiation portion 139. For example, a light-reflecting mirror installed at an angle with respect to a cut surface of the light conveying portion 150 (a cut surface provided perpendicular to the axis O direction) may be used as the light irradiation portion 139. For example, the light conveying portion 150 may be joined to the outer surface of the main body portion 210 without being inserted into the main body portion 210.

For example, the light transmitting portion 239 may be formed by reducing the thickness of one portion of the main body portion 210. For example, the axis O direction (X-axis direction) area in which the light transmitting portion 239 is provided, and the circumferential direction (YZ-axis direction) area in which the light transmitting portion 239 is provided may be arbitrarily changed, and may be longer or shorter than the length illustrated in FIG. 12. For example, the catheter 2 may further include a separate marker portion arranged on the distal end side of the light transmitting portion 239.

Modification Example 4

The configurations of the light irradiation devices 1, 1A to 1J, and the catheters 2 and 2H of the first to tenth embodiments, and the configurations of the light irradiation devices 1, 1A to 1J, and the catheters 2 and 2H of modification examples 1 and 2 may be combined as appropriate. For example, in the light irradiation device 1G described in the eighth embodiment (FIG. 11), at least one of the marker portions 131, 131D and 131E, the distal end side marker portions 132 and 132C, the proximal end side marker portions 133 and 133C, and the distal tip 120F described in the second to seventh embodiments may be provided. The light irradiation system described in the ninth and tenth embodiments may include the light irradiation devices 1A to 1J described in the second to eighth and eleventh embodiments.

Although the aspects have been described based on the embodiments and the modification examples, the embodiments of the above-described aspects are for facilitating understanding of the aspects, and do not limit the aspects. The aspects can be modified and improved without departing from the spirit of the aspects and the scope of the claims, and equivalent aspects are included in the aspects. Further, unless the technical features are described as essential in the present specification, they may be omitted as appropriate.

DESCRIPTION OF REFERENCE NUMERALS 1, 1A-J Light irradiation device
2, 2H Catheter
3 Laser light generator
110, 110G Main body portion
120, 120F, G Distal tip
131, 131D, E Marker portion
132, 132C Distal end side marker portion
133, 133C Proximal end side marker portion
139, 139F Light irradiation portion
140 Connector
141 Connection portion
142 Blade
150 Light conveying portion
161 Marker portion
210 Main body portion
220 Distal tip
231, 261 Distal end side marker portion
232, 262 Proximal end side marker portion
239 Light transmitting portion
240 Connector
241 Connection portion
242 Blade portion

What is claimed is:

1. A medical light irradiation device comprising:
an elongated main body portion;
a light irradiation portion which is provided on one portion of a side surface on a distal end side of the main body portion, and which is configured to irradiate light towards outside of the light irradiation device; and
a marker portion which is provided on the distal end side of the main body portion, wherein the marker portion is radiopaque and has a shape for identifying a location of the light irradiation portion in a circumferential direction of the light irradiation device when viewed from the outside, wherein
the shape of the marker portion is spiral and extends in an axial direction of the light irradiation device.

2. The light irradiation device according to claim 1, further comprising a radiopaque distal end side marker portion provided on a distal end side of the marker portion.

3. The light irradiation device according to claim 2, further comprising
a radiopaque proximal end side marker portion provided on a proximal end side of the marker portion.

4. The light irradiation device according to claim 2, wherein
the main body portion has an elongated tube shape having an inner cavity, and the marker portion is embedded in a tube wall of the main body portion.

5. The light irradiation device according to claim 4, further comprising
a light conveying portion which is embedded in the tube wall and extends from the distal end side to a proximal end side of the main body portion, wherein
the light conveying portion is connected to a light source on the proximal end side of the main body portion, and
the light irradiation portion is arranged on a distal end portion of the light conveying portion, and irradiates light transmitted by the light conveying portion to the outside.

6. The light irradiation device according to claim 1, further comprising a radiopaque proximal end side marker portion provided on a proximal end side of the marker portion.

7. The light irradiation device according to claim 6, wherein
the main body portion has an elongated tube shape having an inner cavity, and the marker portion is embedded in a tube wall of the main body portion.

8. The light irradiation device according to claim 7, further comprising
a light conveying portion which is embedded in the tube wall and extends from the distal end side to a proximal end side of the main body portion, wherein
the light conveying portion is connected to a light source on the proximal end side of the main body portion, and
the light irradiation portion is arranged on a distal end portion of the light conveying portion, and irradiates light transmitted by the light conveying portion to the outside.

9. The light irradiation device according to claim 1, wherein
the main body portion has an elongated tube shape having an inner cavity, and the marker portion is embedded in a tube wall of the main body portion.

10. The light irradiation device according to claim 9, further comprising
a light conveying portion which is embedded in the tube wall and extends from the distal end side to a proximal end side of the main body portion, wherein
the light conveying portion is connected to a light source on the proximal end side of the main body portion, and
the light irradiation portion is arranged on a distal end portion of the light conveying portion, and irradiates light transmitted by the light conveying portion to the outside.

11. A light irradiation system comprising:
the light irradiation device according to claim 1; and
an elongated tube-shaped catheter for inserting the light irradiation device, the catheter having a light transmitting portion provided on at least one portion of a side surface on a distal end side that transmits light inside the catheter to the outside.

12. The light irradiation device according to claim 1, wherein
the marker portion includes at least one wire.

13. The light irradiation device according to claim 1, wherein
the marker portion has a first end positioned at a predetermined angle relative to the light irradiation portion in the circumferential direction.

14. The light irradiation device according to claim 1, wherein
the light irradiation portion is not provided on the entirety of the side surface.

* * * * *